(12) United States Patent
Chen et al.

(10) Patent No.: US 8,278,446 B2
(45) Date of Patent: Oct. 2, 2012

(54) PROCESS FOR PREPARING SUBSTITUTED DIAMINOPYRIMIDINE OXIMES

(75) Inventors: Hongfeng Chen, Somerville, NJ (US); Peter J. Connolly, New Providence, NJ (US); Kirk L. Sorgi, Doylestown, PA (US); Anusuya Choudhury, Churchville, PA (US); Christopher N. Nilsen, Branchburg, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 845 days.

(21) Appl. No.: 11/766,257

(22) Filed: Jun. 21, 2007

(65) Prior Publication Data

US 2008/0249304 A1    Oct. 9, 2008

Related U.S. Application Data

(63) Continuation-in-part of application No. 11/609,450, filed on Dec. 12, 2006.

(60) Provisional application No. 60/752,633, filed on Dec. 21, 2005.

(51) Int. Cl.
| | |
|---|---|
| C07D 239/48 | (2006.01) |
| C07D 239/50 | (2006.01) |
| C07D 401/12 | (2006.01) |
| C07D 401/14 | (2006.01) |
| C07D 403/12 | (2006.01) |
| C07D 403/14 | (2006.01) |

(52) U.S. Cl. ..................................... 544/326; 544/328
(58) Field of Classification Search .................. 544/326, 544/328

See application file for complete search history.

(56) References Cited

U.S. PATENT DOCUMENTS

| 6,080,750 A * | 6/2000 | Hisaki et al. .................. 514/275 |
| 8,013,153 B2 | 9/2011 | Butler et al. |
| 8,153,791 B2 | 4/2012 | Xu et al. |
| 2003/0060466 A1 | 3/2003 | Binggeli et al. |
| 2003/0139435 A1 | 7/2003 | Ahmed et al. |
| 2005/0261313 A1 | 11/2005 | Askew et al. |

OTHER PUBLICATIONS

PCT International Search Report, date Oct. 3, 2007, for PCT Int'l. Appln. No. PCT/US06/61890.
Barillari, Caterina et al., "Solid Phase Synthesis of Diamino-Substituted Pyrimidines", Eur. J. Org. Chem., 2001, pp. 4737-4741.
Abdel-Razik, H., et al. "Synthesis of Some New 2,6-Diamino-4-(P-Arylazo) Anilinopyrimidine and Some Related 5-Arylazopyrimidine Derivatives for Dyeing Synthetic Fibres", Heterocyclic Communications,7(3): 263-270 (2001).
Chapman, N., et al. "Nucleophilic Displacement Reactions in Aromatic Systems", J. Chem. Soc. 1190-1196 (1954).
Gomtsyan, A, et al. "Design, Synthesis, and Structure—Activity Relationship of 6-Alkynlpyrimidines as Potent Adenosine Kinase Inhibitors", J. Med. Chem. (45) p. 3639-3648 (2002).
Hartung, C., et al. "Efficient Microwave-Assisted Synthesis of Highly Functionalized Pyrimidine Derivatives", Tetrahedron, (62), p. 10055-10064 (2006).
Maggiolo, A, et al. "The Reaction of Alkylamines With Chloroheterocyclic Compounds II.[1] 2-Amino-4-Chlor-6-Methylprimdine", J.Am. Chem. Soc. p. 376-382, (1950).
Maggiolo, A., et al. "Synthesis of 2-Methyl-4-Amino-6-Subsittuted Aminopyrimidines", J. Americ. Chem. Socieity, vol. 73, p. 106-107 (1951).
O'Brien, D., et al. "Pyrimidines, VII.2-Amino-4-(Substituted Anilino) Pyrimidines", J. of Organic Chemistry (24) p. 4737-4741 (2001).

* cited by examiner

*Primary Examiner* — Venkataraman Balasubramanian
(74) *Attorney, Agent, or Firm* — Woodcock Washburn LLP

(57) ABSTRACT

The present invention is directed to a process for chemoselective substitution on a halopyrimidine carboxaldehyde having multiple reactive sites and subsequent stereoselective oxime formation.

52 Claims, No Drawings

PROCESS FOR PREPARING SUBSTITUTED DIAMINOPYRIMIDINE OXIMES

CROSS REFERENCE TO RELATED APPLICATIONS

This present application is a Continuation-In-Part of U.S. Nonprovisional patent application Ser. No. 11/609,450, filed Dec. 12, 2006, claiming benefit of U.S. Provisional Patent Application Ser. No. 60/752,633, filed Dec. 21, 2005, which are incorporated herein by reference in its entirety and for all purposes.

FIELD OF THE INVENTION

The present invention is directed to a process for substitution on a pyrimidine compound having multiple reactive sites. More particularly, the process is directed to a chemoselective coupling of an aniline compound with a chlorinated pyrimidine aldehyde compound followed by stereoselective oxime formation.

BACKGROUND OF THE INVENTION

Certain oxime substituted pyrimidines are registered by the Chemical Abstracts Services (CAS) such as 4,6-diamino-5-pyrimidinecarboxaldehyde oxime (CAS Registry No.: 109831-69-8) and N,N'-dimethyl-5-[(methylimino)methyl]-4,6-pyrimidinediamine (CAS Registry No.: 14160-97-5) and described in *Heterocycles*, 1987, 25(1), 343-5. Certain references describe substituted pyrimidine compounds such as United States patents: U.S. Pat. Nos. 6,080,750, 6,107,301 and 6,833,378.

The preparation of various 2,4,6-substituted pyrimidines is described in O'Brien D E, Baiocchi F, Robins R and Cheng C C, Pyrimidines. VII. 2-Amino-4-(Substituted Anilino)Pyrimidines, *Journal of Organic Chemistry*, 1962, 27, 1104-7.

The solid phase synthesis of various diamino-substituted pyrimidines is described in Barillari C., Barlocco D. and Raveglia L. F., Solid Phase Synthesis of Diamino-Substituted Pyrimidines, *European Journal of Organic Chemistry*, 2001, (24), 4737-4741.

The condensation of a 2,6-diamino-4-chloro-pyrimidine with an aminoazobenzene and subsequent coupling of the product with diazotized arylamines is described in Abdel-Razik H. H., Refat H. M. and Zaki, M. E. A., Synthesis of Some New 2,6-Diamino-4-(p-Arylazo)Anilinopyrimidine and Some Related 5-Arylazopyrimidine Derivatives for Dyeing Synthetic Fabrics, *Heterocyclic Communications*, 2001, 7 (3), 263-270.

Nucleophilic aromatic substitution has been used as a general approach for the synthesis of pyrimidine derivatives from halopyrimidines (as described in Gomtsyan A, Didomenico S, Lee C-Hung, Matulenko M A, Kim K, Kowaluk E A, Wismer C T, Mikusa J, Yu H, Kohlhaas K, Jarvis M F, Bhagwat S S, Design, Synthesis, and Structure-Activity Relationship of 6-Alkynylpyrimidines as Potent Adenosine Kinase Inhibitors, *J. Med. Chem.* 2002, 45 (17), 3639-3648; Chapman N B, Rees C W, Nucleophilic displacement reactions in aromatic systems. III. Kinetics of the reactions of chloronitropyridines and chloropyrimidines with piperidine, morpholine, pyridine, and aniline, *J. Chem. Soc.* 1954, 1190-6; Hartung C H, Backes A C, Beatrice F, Missio A, Philipp A, Efficient microwave-assisted synthesis of highly functionalized pyrimidine derivatives, *Tetrahedron*, 2006, 62, 10055-10064; and Maggiolo A, Phillips A P, Hitchings G H, Synthesis of 2-methyl-4-amino-6-(substituted-amino) pyrimidines, *J. Am. Chem. Soc.*, 1951, 73, 106-7).

The hydrolysis of chloropyrimidines to hydroxyl pyrimidines in strong hydrochloric acid solutions at elevated temperature has also been described (see Maggiolo A and Phillips A P, *J. Org. Chem.* 1951, 16. 376-382).

Accordingly, there remains a need for a process to selectively displace a halogen atom on an aldehyde-substituted pyrimidine with an amine nucleophile.

SUMMARY OF THE INVENTION

The present invention is directed to a process for preparing a compound of Formula (I):

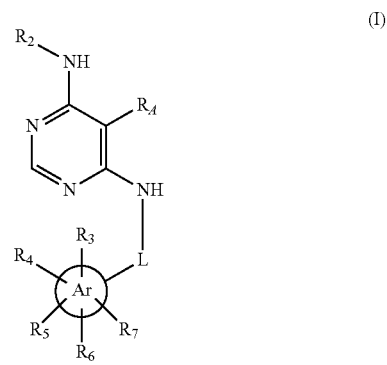

wherein $R_4$, $R_2$, $R_3$, $R_4$, $R_5$, $R_6$, $R_7$, L and Ar are as defined herein.

The process of the present invention is a chemoselective coupling of an aniline compound and a halogenated pyrimidine carboxaldehyde to provide an intermediate that does not require isolation followed by stereoselective oxime formation.

The process can efficiently provide a free base, a mono-acid or bis-acid salt, particularly a mono-hydrochloride salt, of the compound of Formula (I). The mono-acid can be provided by stoichiometrically conserving the in situ acid.

This method is beneficial since toxic starting materials and reagents such as mutagenic hydroxylamine, chloro-ethylmorpholine and cesium carbonate, as used in previous synthesis methods, are avoided. The process of the present invention enables the desired final product to be obtained by direct crystallization substantially free of organic solvent.

Accordingly, the process invention does not lead to production of residues that are hazardous to the environment.

DETAILED DESCRIPTION OF THE INVENTION

The present invention is directed to a process for preparing a compound of Formula (I) and an acid salt thereof:

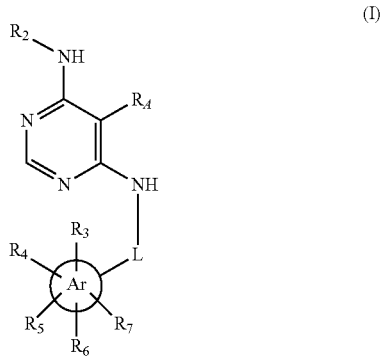

(I)

wherein

L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl;

$R_A$ is selected from C=N—O—$R_1$;

$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein aryl, aryloxy, aryl-amino, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The process of the present invention comprises the steps of:

Scheme A

Step 1. reacting a Compound 1a** (wherein Ra represents a halogen leaving group), a Compound A1 in an aqueous solvent and a catalytic amount of acid (wherein the acid is preferably an acid wherein the anion is a halide that matches the Ra halogen leaving group) to provide a Compound A2 acid salt:

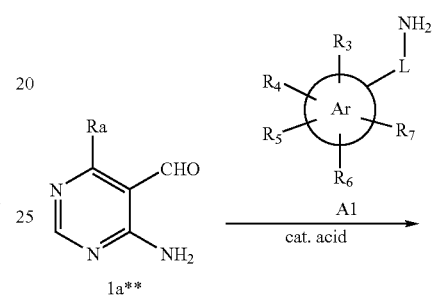

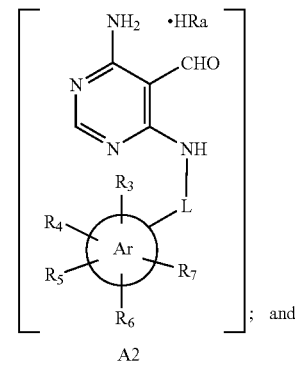

Step 2. reacting the Compound A2 acid salt with a Compound A3 bis-acid salt (wherein the acid of the bis-acid salt may be HRa) and a base to provide a Compound A4 acid salt, representative of a compound of Formula (I):

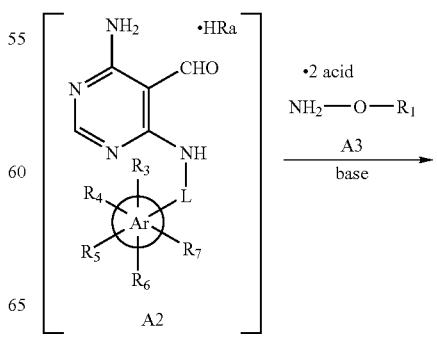

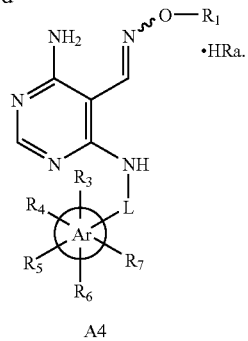

An example of the present invention includes a process wherein a mixture of geometric isomers of the Compound A4 may be formed, in particular, a mixture of geometric isomers consisting of a Compound A4 E-isomer and a corresponding Z-isomer.

An example of the present invention includes a process wherein the Compound A4 E-isomer is obtained.

An example of the present invention includes a process wherein one of the solvents used in Step 1 of the reaction is water and the other is optionally selected from isopropanol, 2-methoxy-ethanol, 1-propanol, methanol, ethanol, 1-butanol, THF, 2-Me-THF, toluene or acetonitrile.

An example of the present invention includes a process wherein one of the solvents used in Step 1 is water and the other is optionally selected from isopropanol, 2-methoxy-ethanol, 1-propanol or acetonitrile.

An example of the present invention includes a process wherein the solvent used in Step 1 is water.

An example of the present invention includes a process wherein the solvent used in Step 1 is water and the other is 2-methoxy-ethanol.

An example of the present invention includes a process wherein the amount of water is at least 0.005 molar equivalents (wherein the molar equivalence is based on Compound A1).

An example of the present invention includes a process wherein the amount of water is in a range of from about 1 molar equivalent to about 99 molar equivalents (wherein the molar equivalence is based on Compound A1).

An example of the present invention includes a process wherein the amount of water is in a range of from about 1 molar equivalent to about 26 molar equivalents (wherein the molar equivalence is based on Compound A1).

An example of the present invention includes a process wherein the amount of water is in a range of from about 1 molar equivalent to about 13 molar equivalents (wherein the molar equivalence is based on Compound A1).

An example of the present invention includes a process wherein the amount of solvent and the amount of water used in Step 1 are in a ratio, wherein the ratio is in a range of from 6:5 (v/v) to about 11:1 (v/v) solvent:water.

An example of the present invention includes a process wherein the solvent to water ratio used in Step 1 is a ratio of about 11:1 (v/v) solvent:water, or is a ratio of about 9:1 (v/v) solvent:water, or is a ratio of about 9:2 (v/v) solvent:water, or is a ratio of about 8:3 (v/v) solvent:water, is a ratio of about 8:2 (v/v) solvent:water, or is a ratio of about 7:4 (v/v) solvent:water, or is a ratio of about 6:5 (v/v) solvent:water.

An example of the present invention includes a process wherein the solvent to water ratio used in Step 1 is a ratio of about 9:1 (v/v) solvent:water.

An example of the present invention includes a process wherein the amount of aqueous solvent is in a range of from about 6 ml to about 76 ml per 1 g of Compound A1.

An example of the present invention includes a process wherein the amount of aqueous solvent is in a range of from about 9 ml to about 11 ml per 1 g of Compound A1.

An example of the present invention includes a process wherein the amount of aqueous solvent is about 10 ml per 1 g of Compound A1.

An example of the present invention includes a process wherein the catalytic amount of acid used is in a range of from about 0.01 molar equivalents to about 2 molar equivalents (wherein the molar equivalence is based on Compound A1).

An example of the present invention includes a process wherein the catalytic amount of acid is in a range of from about 0.01 molar equivalents to about 0.15 molar equivalents (wherein the molar equivalence is based on Compound A1).

An example of the present invention includes a process wherein the catalytic amount of acid is in a range of from about 0.1 molar equivalents to about 0.15 molar equivalents (wherein the molar equivalence is based on Compound A1).

An example of the present invention includes a process wherein the acid used is HCl, wherein Ra in Compound 1a is chloro or, alternatively, HBr, wherein Ra in Compound 1a is bromo.

An example of the present invention includes a process wherein the water and the solvent used in Step 1 are mixed prior to the addition of other reactants, thus forming an aqueous solvent.

An example of the present invention includes a process wherein water and the catalytic amount of acid used in Step 1 are mixed prior to the addition of other reactants, thus forming an aqueous acid.

An example of the present invention includes a process wherein the Compound 1a** and the aqueous solvent are mixed prior to the addition of other reactants.

An example of the present invention includes a process wherein the Compound A1 and the aqueous solvent are mixed prior to the addition of other reactants.

An example of the present invention includes a process wherein Compound 1a**, Compound A1, the aqueous solvent and the catalytic amount of acid are in a mixture and the reaction mixture is stirred at a temperature of about 40° C., then heated to a temperature of about 65° C.

An example of the present invention includes a process wherein a first portion of about 20% of the total amount of Compound A1 is added to a mixture of Compound 1a** and the aqueous solvent and the resulting reaction mixture is stirred at a temperature of about 40° C.; then, a second portion of about 40% of the total amount of Compound A1 is added and the reaction mixture is stirred at a temperature of about 40° C.; and, a third portion of about 40% of the total amount of Compound A1 is added and the reaction mixture is stirred at a temperature of about 40° C., then heated to a temperature of about 65° C.

An example of the present invention includes a process wherein the Compound A2 is isolated as a free base or as a mono-acid salt.

The presence of water in Step 1 reduces the formation of the undesired imine Compounds AA3 and AA4. However, the presence of water in Step 2 may slow the reaction rate and may result in various amounts of the Z-isomer of Compound A4. Water may be removed in Step 2, such as by azeotropic distillation.

In a preferred embodiment of a one-pot synthesis, the solvent selected for use in Step 2 should be substantially the same solvent as that chosen for use in Step 1.

An example of the present invention includes a process wherein the solvent used in Step 2 of the reaction is selected from isopropanol, 2-methoxy-ethanol, 1-propanol, methanol, ethanol, 1-butanol, THF, 2-Me-THF or acetonitrile.

An example of the present invention includes a process wherein the solvent used in Step 2 is selected from isopropanol, 2-methoxy-ethanol, 1-propanol or acetonitrile.

An example of the present invention includes a process wherein the solvent used in Step 2 is 2-methoxy-ethanol.

An example of the present invention includes a process wherein the Compound A2 is a freebase or mono-acid salt and the Compound A3 is a freebase, a mono-acid salt or bis-acid salt.

An example of the present invention includes a process wherein the Compound A2 is a mono-acid salt and the Compound A3 is a bis-acid salt.

An example of the present invention includes a process wherein the Compound A2 mono-acid salt and the Compound A3 bis-acid salt are in about a 1:1 molar equivalent ratio.

An example of the present invention includes a process wherein the base used in Step 2 is present in a stoichiometric amount and, wherein said amount varies upon whether Compound A3 is a freebase, a mono-acid salt or bis-acid salt and whether the reaction product Compound A4 may be a freebase, a mono-acid salt or a bis-acid salt.

An example of the present invention includes a process wherein the base used in Step 2 is present in about 2 molar equivalents.

An example of the present invention includes a process wherein the Compound A2 mono-acid salt, the Compound A3 bis-acid salt and the base are in about a 1:1:2 molar equivalent ratio.

An example of the present invention includes a process wherein the base used in Step 2 is NaOH or $NaHCO_3$.

An example of the present invention includes a process wherein the Compound A4 is obtained as an acid salt precipitate during azeotropic distillation at a temperature in a range of from about 102° C. to about 115° C. and, wherein the distilled liquid is controlled to an amount of about twice the amount of water initially added.

An example of the present invention includes a process wherein the Compound A2 mono-acid salt is reacted with the Compound A3 bis-acid salt and the base at a temperature in a range of from about 106° C. to about 113° C., An example of the present invention includes a process wherein Compound A4 is obtained as a freebase, a mono-acid salt or as a bis-acid salt.

An example of the present invention includes a process wherein the Compound A4 mono-acid salt is recrystallized from a solvent system selected from 1-propanol and water or isopropanol and water, wherein the solvent is in a ratio with water, and wherein the ratio of solvent:water is about 1:1 (v/v).

An example of the present invention includes a process wherein the recrystallization solvent system is 1-propanol and water, wherein 1-propanol is in a ratio with water, and wherein the ratio of 1-propanol:water is about 1:1 (v/v).

An example of the present invention includes a process wherein the compound of Formula (I) and an acid salt thereof is selected from a compound of Formula (Ia):

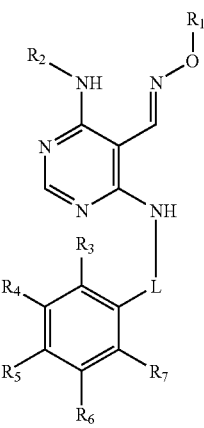

(Ia)

wherein
L is selected from a bond, $C_{1-6}$alkyl or halo-$C_{1-6}$alkyl;
$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;
$R_2$ is selected from hydrogen, $C_{1-8}$alkyl or $C_{1-8}$alkoxy; and
$R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, $C_{3-12}$cycloalkyl, aryl, aryloxy, aryl-amino, aryl-$C_{1-8}$alkyl, aryl-$C_{1-8}$alkoxy, arylcarbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl,
wherein benzofused-heterocyclyl is optionally substituted on the heterocyclyl portion with one or two oxo substituents, and
wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

An example of the present invention includes a process wherein the compound of Formula (I) and an acid salt thereof is selected from a compound of Formula (Ib):

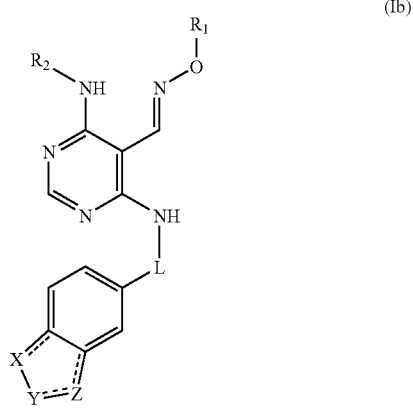

wherein
L is selected from a bond, $C_{1-6}$alkyl or halo-$C_{1-6}$alkyl;
—X—Y—Z— is a moiety selected from —N($R_3$)—N═C($R_3$)—, ═N—N($R_3$)—C($R_3$)═, —N($R_3$)—C($R_3$)═C($R_3$)—, —C($R_3$)$_2$—C($R_3$)$_2$—C($R_3$)$_2$—, —O—C($R_3$)$_2$—O—, —N($R_3$)—C($R_3$)═N—, —O—C($R_3$)═C($R_3$)—, —N($R_3$)—C($R_3$)$_2$—C($R_3$)$_2$— or —S—C($R_3$)═N—;
wherein the dashed lines in formula (Ib) represent the locations for one or two double bonds when present in the moiety;
$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;
$R_2$ is selected from hydrogen, $C_{1-8}$alkyl or $C_{1-8}$alkoxy; and
$R_3$ is selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and
wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

An example of the present invention includes a process wherein the compound of Formula (I) and an acid salt thereof is selected from a compound of Formula (Ic):

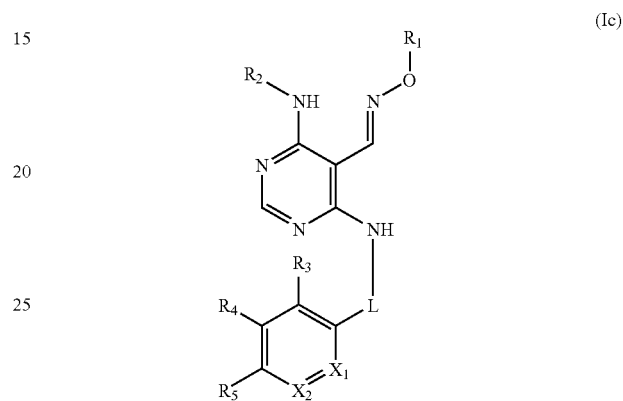

wherein
$X_1$ and $X_2$ is each selected from —C($R_6$)— or —N—, wherein $X_1$ and $X_2$ are not the same;
L is selected from a bond, $C_{1-6}$alkyl or halo-$C_{1-6}$alkyl;
$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;
$R_2$ is selected from hydrogen, $C_{1-8}$alkyl or $C_{1-8}$alkoxy; and
$R_3$, $R_4$, and $R_5$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl; and $R_6$ is selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl or $C_{1-8}$alkyl-amino-$C_{1-8}$alkyl.

The foregoing Scheme A and the other schemes shown herein are offered by way of illustration; the invention should not be construed as being limited by the chemical reactions and conditions expressed. The methods for preparing the various starting materials used in the schemes are within the skill of persons versed in the art.

Discussion of the Problem

Selectivity at a specific site on a molecule possessing multiple sites of reactivity is challenging.

The present invention is generally directed towards a sequential one-pot synthesis. A key attribute of this synthesis is the chemoselective coupling of a substituted aniline with an amino-6-halo substituted pyrimidine-5-carbaldehyde. The competing reactivity of the halogen and carbaldehyde electrophilic centers towards the nucleophilic aniline gives rise to several reactive intermediates AA1 and AA2, (originating from the reaction of the nuclear aldehyde group with the substituted aniline) along with the product A2. This invention shows how the undesired reactive intermediates AA1 and AA2 are siphoned to the desired product A2.

A second key attribute of this synthesis is the reaction of the anilino substituted pyrimidine-5-carbaldehyde with an amine salt to generate the acid salt or the free base of the product with the desired E-selectivity at the oxime-ether linkage.

The challenges were to control the E-oxime-ether formation and selectively prepare the desired salt form. The present invention addresses these challenges to provide a sequential one-pot process which successfully combines both the steps.

Scheme B depicts the displacement of a chloro substituent with an amine on a pyrimidine molecule, which also possesses a reactive aldehyde group, resulting in competition for each reactive site.

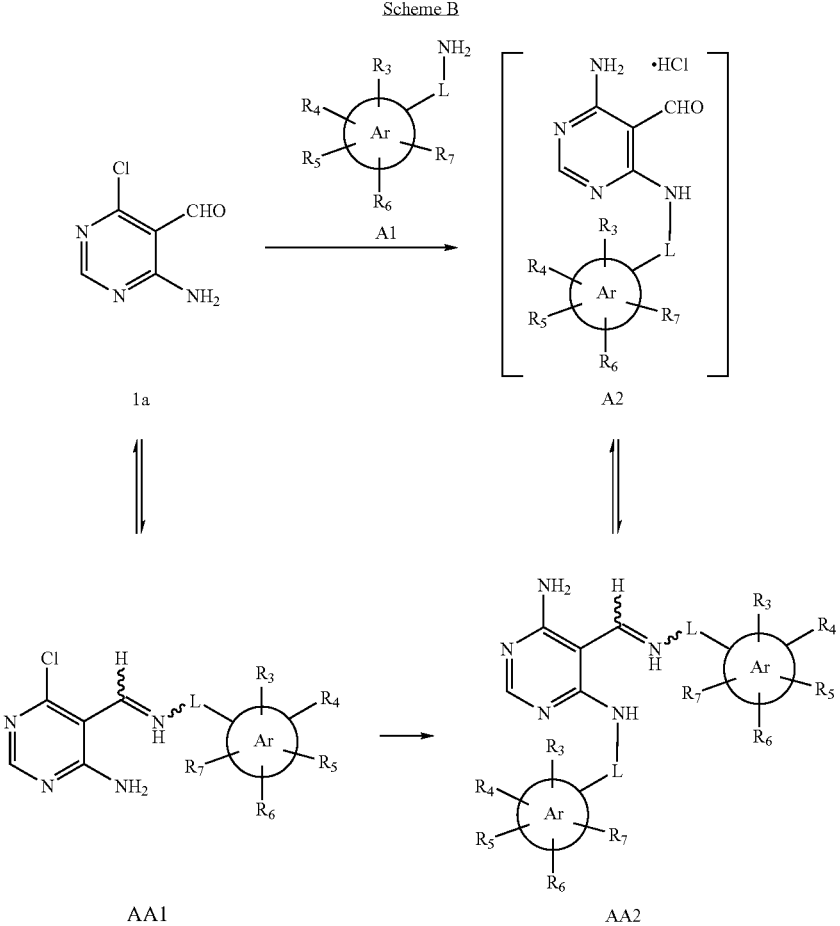

In discovering the process of the present invention, to enable selective substitution on the pyrimidine molecule, certain experimental parameters were explored, including the presence and absence of a base in Step 1 (as described in Scheme C), the presence and absence of an acid in Step 1 (as described in Scheme E), the presence and absence of water, the types of solvents and solvent systems in Step 1 (as described in Scheme C and F), the types of solvents and solvent systems in Step 2 (as described in Scheme D), and process reaction conditions such as temperature (as described in Scheme G).

The reactivity of the amine Compound A1 at the chloro and aldehyde sites on 4-amino-6-chloro-pyrimidine-5-carbaldehyde Compound 1a also produces a certain equivalence of both HCl and water in situ. Although an amount of water and acid is expected to be generated in this reaction step, it was surprising that adding water to the solvent system used in the reaction of Compound 1a and Compound A1 and a catalytic amount of acid would drive the reaction to completion, reverse the equilibrium and converts Compound AA1 to the Compound 1a and Compound A1 starting materials and converts Compound AA2 to the product Compound A2 and Compound A1 starting material.

Scheme C illustrates and Table 1 shows the products obtained in Step 1 (as determined at 230 nm) by reacting the chloro substituted pyrimidine aldehyde Compound 1a (1 mmol) with the substituted aniline Compound 1b (1 mmol) in various solvents and solvent systems with and without water (2.5 ml) and with and without a base, such as TEA (2 Equivalents), at around 62° C.

The amounts (Area %) of Compound 1c, (5E)-N-(4-benzyloxy-3-chloro-phenyl)-5-[(4-benzyloxy-3-chloro-phenylimino)-methyl]-pyrimidine-4,6-diamine Compound AA3 and (5E)-5-[(4-benzyloxy-3-chloro-phenylimino)-methyl]-6-chloro-pyrimidin-4-ylamine Compound AA4 are shown in Table 1. These amounts were obtained about 2 to 3 hours after the reaction was initiated for solvents/systems 3-8 and 10-16; and about 5 hours after reaction initiation for the solvents/systems 1, 2 and 9.

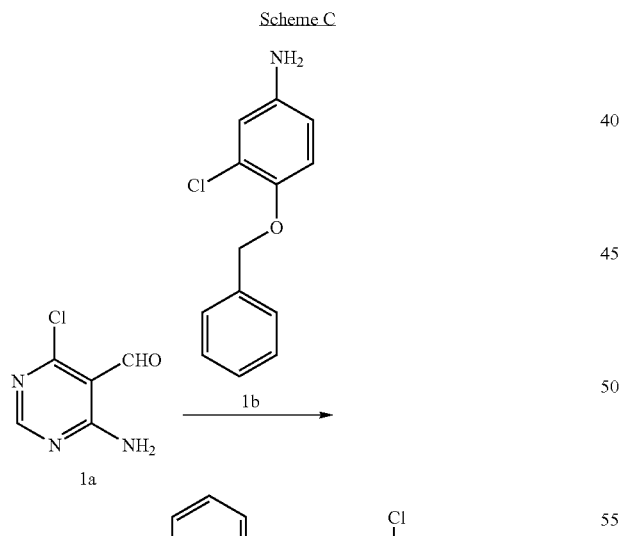

Scheme C

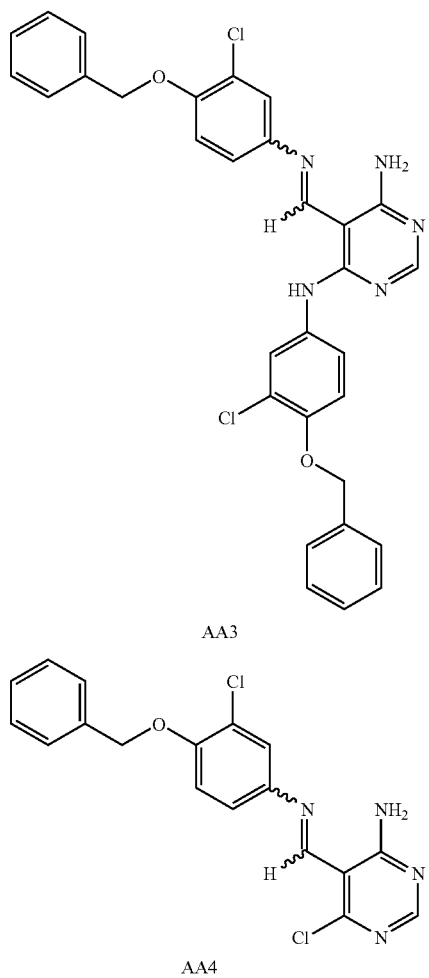

AA3

AA4

Table 1 shows the influence of the various solvents/systems on the products produced in reaction Scheme C.

TABLE 1

| System | Solvent | Cpd 1a | Cpd 1b | Cpd 1c | Cpd AA3 | Cpd AA4 |
|---|---|---|---|---|---|---|
| 1 | MeOH/TEA | 17.4 | 10.24 | 70.44 | 1.00 | 0.9 |
| 2 | IPA/TEA | 9.5 | 4.62 | 83.5 | 1.7 | 0.6 |
| 3 | 2-Me-THF/TEA | 56.3 | 31.9 | 9.14 | 1.3 | 1.4 |
| 4 | THF/TEA | 54.0 | 31.26 | 10.5 | 2.24 | 1.95 |
| 5 | NMP/TEA | 11.2 | 34.4 | 49.8 | 2.85 | 1.6 |
| 6 | DMF/TEA | 30.0 | 16 | 47.0 | 4.7 | 1.8 |
| 7 | ACN/TEA | 46.3 | 26.7 | 18.7 | 2.5 | 0.6 |
| 8 | Acetone/TEA | 51.8 | 29.2 | 12.56 | 5.6 | 0.8 |
| 9 | 1-propanol/TEA | 6.66 | 5.0 | 81.9 | 6.4 | 2.7 |
| 10 | IPA | 37.5 | 1.49 | 19.1 | 22.4 | 4.4 |
| 11 | IPA/water | 0.75 | 3.0 | 85.3 | 11.0 | nd |
| 12 | IPA/HCl (1.5 eq) | nd | 10 | 78 | 14 | nd |
| 13 | IPA/HCl/water | nd | 1.03 | 98.23 | 0.7 | nd |
| 14 | 2-OMe-EtOH/HCl/water | 0.37 | 1.61 | 94 | nd | 0.25 |
| 15 | water/HCl | nd | nd | 62.9 | 37.1 | nd |
| 16 | toluene/HCl/water | 11.0 | 2.48 | 72 | 0.63 | 0.34 |
| 17 | ACN/HCl/water | 0.76 | 0.79 | 98 | nd | 0.85 |

Scheme D illustrates that certain solvents and bases used in Step 2 also influenced the type of oxime form produced.

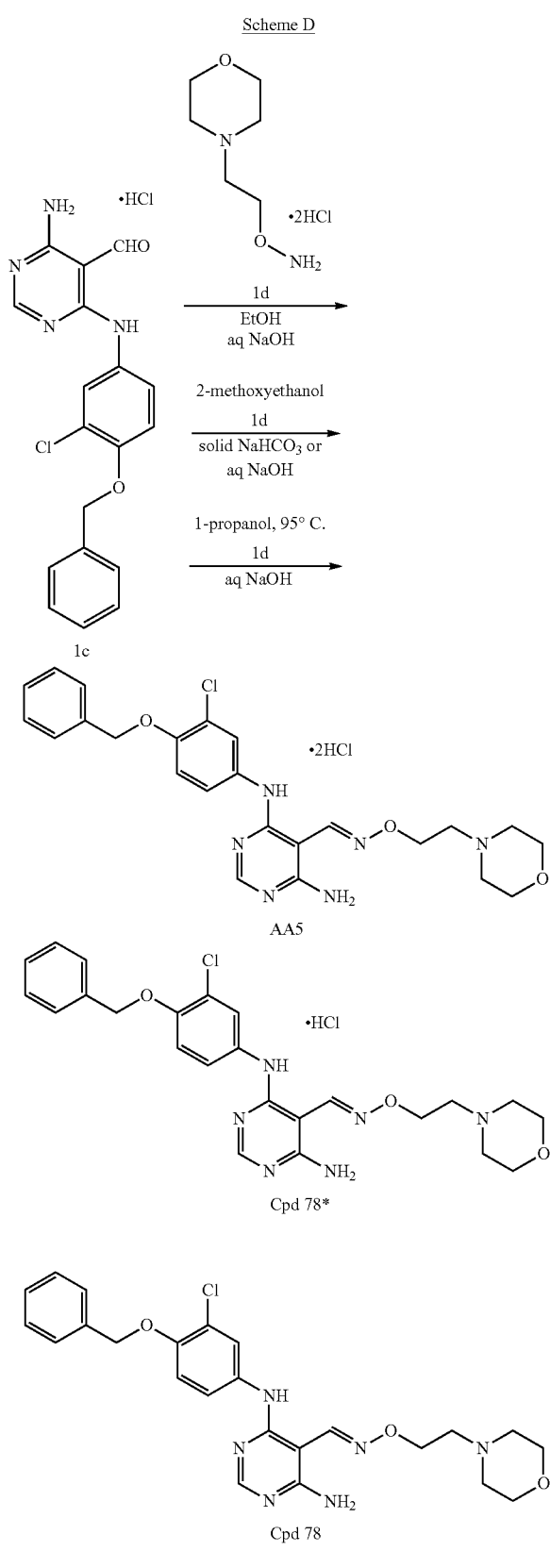

Scheme D pyrimidine-5-carbaldehyde O-(2-morpholin-4-yl-ethyl)-oxime bis-hydrochloride salt Compound AA5 was in a range of about 85% yield.

When a 2-OMe-EtOH and NaHCO$_3$ (2 Equiv.) solvent system was used, the yield of the desired product mono-hydrochloride salt Compound 78* was in a range of about 90% yield.

When a 1-propanol and aqueous NaOH (3 Equiv.) solvent system was used, the product Compound 78 was obtained as a free base in a range of about 85% yield.

Additionally, as shown in Table 2, the use of certain amounts of base influenced the type of salt produced.

TABLE 2

| System | Solvent | Salt Form Produced |
|---|---|---|
| 1 | <2 Eq. of base | mixture of AA5 and Cpd 78* |
| 2 | 2 Eq. of base | Cpd 78* only |
| 3 | >2 Eq. of base | mixture of Cpd 78 and Cpd 78* |

Moreover, the use of certain solvents influenced whether the E or Z geometric isomers was produced.

Table 3 shows the influence of various solvents used in the reaction on the ratio of E or Z geometric isomers obtained.

TABLE 3

| System | Solvent | Ratio of E:Z Isomer |
|---|---|---|
| 1 | 1-propanol | 97:1 |
| 2 | IPA | 33:1 |
| 3 | EtOH | 3.3:1 |
| 4 | MeOH | 3:1 |
| 5 | 2-OMe-EtOH | 98:1 |

As well, the presence of water in the oxime formation step slowed the reaction rate and resulted in formation of a higher amount of the Z isomer. The removal of water in the oxime formation step converted the majority of the Z isomer to the E isomer.

Scheme E illustrates that, in Step 1, the addition of 6N HCl (10-15% mol) completed the reaction of Compound 1a and Compound 1b to provide Compound 1c as the predominant product as determined by HPLC Area % analysis (at 277 nm).

Scheme E

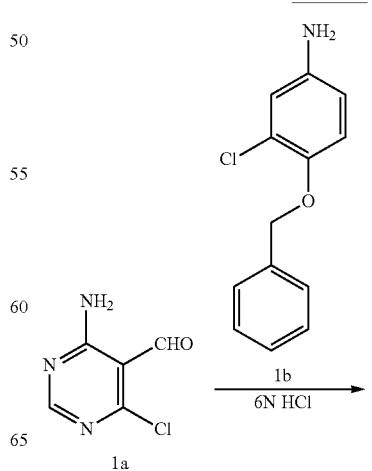

When EtOH and aqueous NaOH (1 Equiv.) were used for reacting Compound 1c and Compound 1d, the yield of the product of 4-amino-6-(4-benzyloxy-3-chloro-phenylamino)-

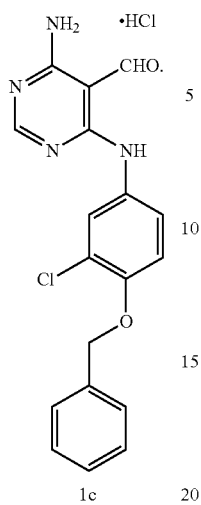

1c

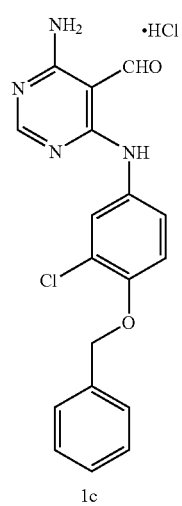

1c

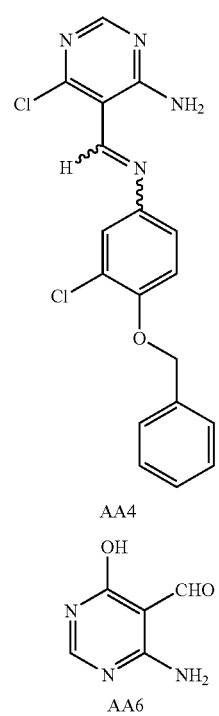

AA4

Scheme F illustrates and Table 4 shows the products formed depending on the use of certain solvent systems and the amount of acid. Compound 1a (1.10 Eq) with Compound 1b (1.00 Eq) were reacted in various aqueous solvents and solvent systems (10 ml per 1 g of Compound 1b) and a catalytic amount of HCl at 80° C. The amount of each product (5E)-5-[(4-benzyloxy-3-chloro-phenylimino)-methyl]-6-chloro-pyrimidin-4-ylamine Compound AA4 and 4-amino-6-hydroxy-pyrimidine-5-carbaldehyde Compound AA6 (Area % compared to Compound 1c, as determined at 220 nm) shown in Table 4 was obtained 4 hours after the reaction was initiated.

AA6

Certain solvent systems tested were not scalable because at certain temperatures the mixture became a very thick, unstirrable slurry. Comparatively, the 2-OMe-EtOH:H$_2$O system, having a 9:1 ratio of solvent to water produced an optimal solution.

Scheme F

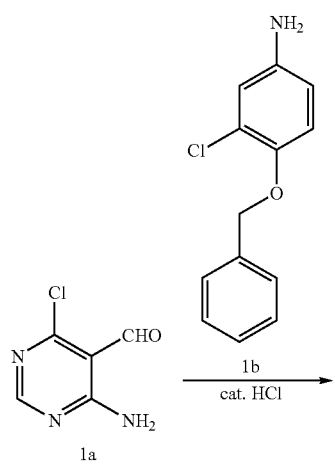

TABLE 4

| Solvent System | 6 N HCl | Cpd 1a | Cpd 1b | Cpd 1c | Cpd AA3 | Cpd AA4 | Cpd AA6 |
|---|---|---|---|---|---|---|---|
| 2-OMe-EtOH:H$_2$O, 8:2 | 0.1 Eq (36 uL) | 0.14 | 2.35 | 91.4 | nd | 0.60 | 5.7 |
| 2-OMe-EtOH:H$_2$O, 8:2 | 0.15 Eq (53 uL) | 0.10 | 1.37 | 94.2 | nd | 0.27 | 4.07 |
| ACN:H$_2$O, 11:1 | 0.1 Eq (36 uL) | 1.17 | 0.63 | 97.6 | nd | 0.50 | nd |

TABLE 4-continued

| Solvent System | 6 N HCl | Cpd 1a | Cpd 1b | Cpd 1c | Cpd AA3 | Cpd AA4 | Cpd AA6 |
|---|---|---|---|---|---|---|---|
| ACN:H$_2$O, 11:1 | 0.15 Eq (53 uL) | 0.76 | 0.79 | 97.6 | nd | 0.85 | nd |
| 2-OMe-EtOH:H$_2$O, 9:1 | 0.15 Eq (53 uL) | 0.30 | 1.60 | 93.8 | nd | 0.20 | 3.50 |

Scheme G illustrates the products obtained by the effect of temperature on the reaction at each step. Table 5 and 6 show (in Area %) the amounts of Compound 1c and 4-amino-6-hydroxy-pyrimidine-5-carbaldehyde Compound AA6 produced in Step 1, and the amount of 4-amino-6-(4-benzyloxy-3-chloro-phenylamino)-pyrimidine-5-carbonitrile Compound 118 produced in Step 2, each at certain temperatures. The analysis indicates that Step 1 should be run at a lower temperature than Step 2.

Scheme G

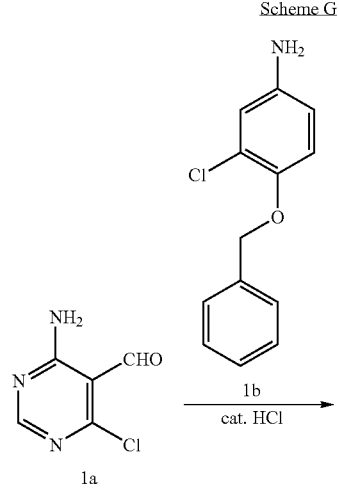

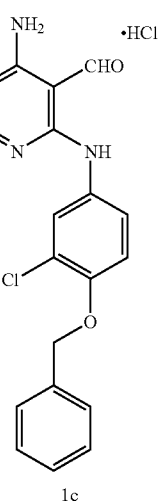

1c

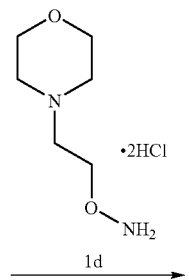

1d

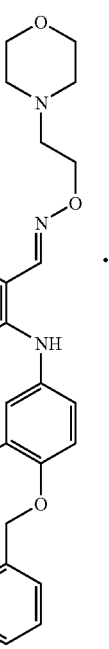

Cpd 78*

+

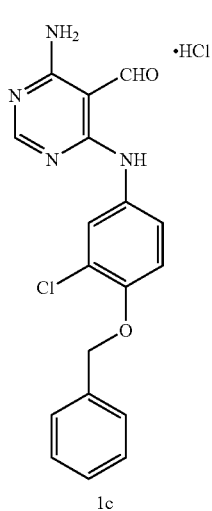 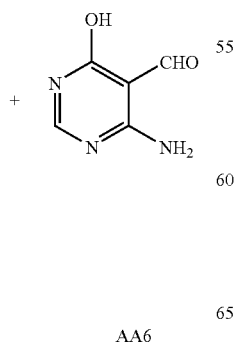

1c                    AA6

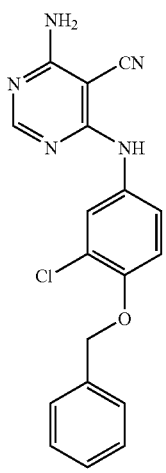

118

Compound 1a was reacted with Compound 1b in an aqueous solution of 2-OMe-EtOH in the presence of a catalytic amount of HCl (0.1 Eq) at an optimum temperature of about 65° C.

TABLE 5

|  | Product | Temperature (° C.) | | |
|---|---|---|---|---|
|  |  | 65 | 80 | 95 |
| Step 1 | Cpd 1c | 99 | 94 | 94 |
|  | Cpd AA6 | approx. 1 | approx. 3 | approx. 3 |

Compound 1c was reacted with Compound 1d in 2-OMe-EtOH and solid NaHCO$_3$ or aqueous NaOH and the Compound 78* mono-hydrochloric acid salt was obtained as a precipitate during azeotropic distillation at a temperature of between about 102° C. to about 115° C., wherein the distilled liquid is controlled to an amount of about twice the amount of water present in the reaction.

The HPLC Area % of Compound 118 increased as temperature was increased or when insufficient solvent was present. The amount of Compound 118 was controlled by maintaining temperature to between about 102° C. to about 115° C. and by distilling an amount of water-solvent mixture that was equal to twice the amount of water originally added, thus substantially removing all the water.

The HPLC Area % of the Z-isomer of Compound 78* as shown in Table 6 was higher at lower reaction temperatures. As reaction temperatures were increased or when the reaction was allowed to run longer at an elevated temperature, the Z-isomer converted to the desired E-isomer of Compound 78*.

For example, at 95° C. and at 107° C. the presence of the Z-isomer resulted in a less than optimum yield of the E-isomer Compound 78*. Although, at those temperatures, the level of Compound 118 was low. At a temperature of 113° C., conversion of the Z-isomer to the E-isomer resulted in an increased yield of Compound 78*, even though the level of Compound 118 at that temperature was higher.

TABLE 6

|  | Product | Temperature (° C.) | | |
|---|---|---|---|---|
|  |  | 95 | 107 | 113 |
| Step 2 | Cpd 78* | 94 | 96 | 96 |
|  | Cpd 118 | <0.1 | 0.4 | 2.7 |

Table 7 shows the reaction mixture observed by reacting Compound 1a (1.55 g, 1.07 Eq) with Compound 1b (2.00 g) in one portion in an aqueous solution of 2-OMe-EtOH (11 ml per 1 g of Compound 1b) in the presence of a catalytic amount of HCl (0.14 ml, 0.1 Eq), wherein the ratio of 2-OMe-EtOH and water and the temperature at which the HCl was added were varied. Based on the observations shown in Table 7, reacting Compound 1a and Compound 1b in one portion resulted in a suboptimal mixture. As a result, Compound 1b was added in various portions until an optimal mixture was obtained.

TABLE 7

| Amt of 2-OMe-EtOH (ml) | Amt of Water (ml) | Temperature | Mixture |
|---|---|---|---|
| 18 | 4 | RT | yellow slurry, upon heating became a solution, then a gel |
| 18 | 4 | 50° C. | yellow slurry, upon heating became a gel |
| 16 | 6 | RT | yellow slurry, upon heating became a solution, then a gel |
| 16 | 6 | 50° C. | same as above |
| 14 | 8 | RT | yellow slurry, upon heating became a gel |
| 14 | 8 | 50° C. | same as above |
| 12 | 10 | RT | same as above |
| 12 | 10 | 50° C. | same as above |

The recrystallization of Compound 78* from an organic solvent as a precipitate substantially free of solvent required analysis of various solvent systems, the results of which are shown in Table 8. The solvents in each system are present in a ratio with water of 1:1 (v/v), the yield and residual solvent are shown in percent (%). As generally seen in Table 8, the recrystallized product upon drying showed residual solvent content. However, the nPA:H$_2$O solvent system optimally provided a higher yield with a lower level of residual solvent.

TABLE 8

| System | Yield | Residual Solvent |
|---|---|---|
| MeOH:H$_2$O | approx. 90 | 0.22 MeOH |
| EtOH:H$_2$O | approx. 90 | 0.67 EtOH |
| nPA:H$_2$O | approx. 90 | 0.29 nPA, was reduced to 870 ppm when drying time was extended |
| iPA:H$_2$O | approx. 90 | 0.15 iPA |
| iPA:H$_2$O | approx. 70-76 | 0.03 iPA, with azeotropic removal of iPA |
| ACN:H$_2$O | approx. 70 | 0.024 ACN, with azeotropic removal of ACN |

Scheme H illustrates the process of the present invention directed to preparing a Compound 78** acid salt of the formula:

Scheme H

Cpd 78**

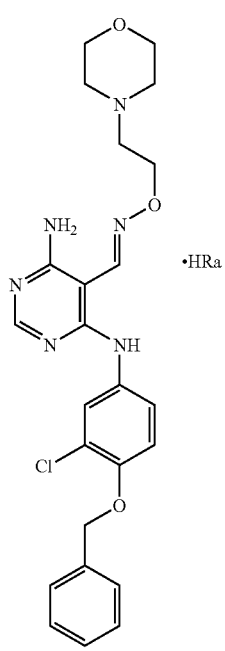

comprising the steps of:

Step 1. reacting a Compound 1a (wherein Ra represents a halogen leaving group), a 4-benzyloxy-3-chloro-phenylamine Compound 1b in an aqueous solvent and a catalytic amount of acid (wherein the acid is preferably an acid wherein the anion is a halide that matches the Ra halogen leaving group) to provide a Compound 1c acid salt:

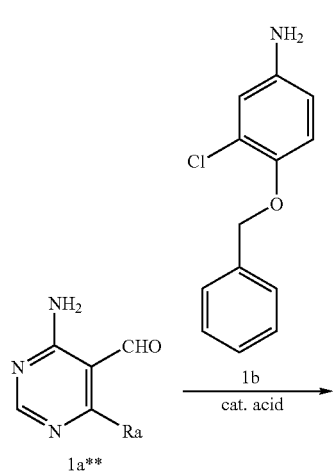

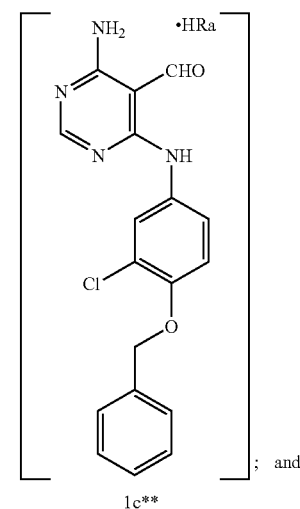

Step 2. reacting the Compound 1c acid salt with a Compound 1d bis-acid salt (wherein the acid of the bis-acid salt may be HRa) and a base to provide a Compound 78** acid salt, representative of a compound of Formula (I):

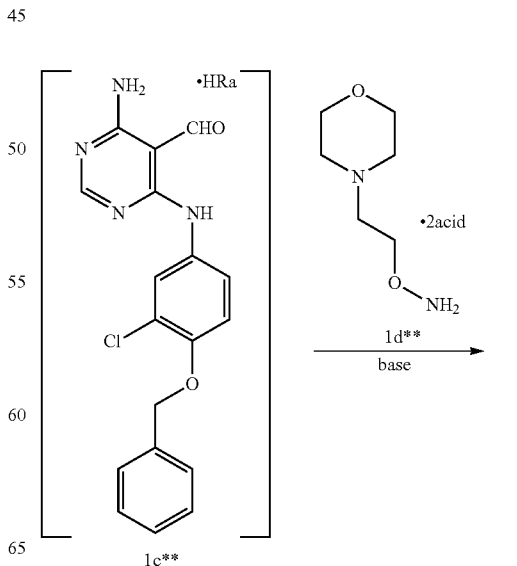

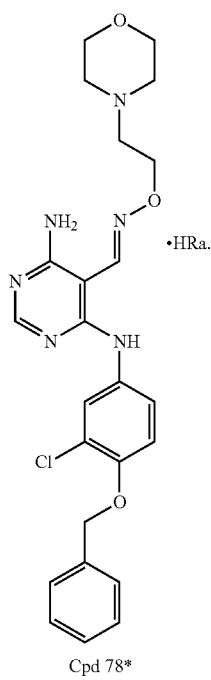

Cpd 78*

An example of the present invention includes a process wherein a mixture of geometric isomers of Compound 78 may be formed, in particular, a mixture of geometric isomers consisting of a Compound 78 E-isomer and a corresponding Z-isomer.

An example of the present invention includes a process wherein the Compound 78** E-isomer is obtained.

An example of the present invention includes a process wherein one of the solvents used in Step 1 of the reaction is water and the other is optionally selected from isopropanol, 2-methoxy-ethanol, 1-propanol, methanol, ethanol, 1-butanol, THF, 2-Me-THF, toluene or acetonitrile.

An example of the present invention includes a process wherein one of the solvents used in Step 1 is water and the other is optionally selected from isopropanol, 2-methoxy-ethanol, 1-propanol or acetonitrile.

An example of the present invention includes a process wherein the solvent used in Step 1 is water.

An example of the present invention includes a process wherein the solvent used in Step 1 is water and the other is 2-methoxy-ethanol.

An example of the present invention includes a process wherein the amount of water used is at least 0.005 molar equivalents (wherein the molar equivalence is based on Compound 1b).

An example of the present invention includes a process wherein the amount of water used is in a range of from about 1 molar equivalent to about 99 molar equivalents (wherein the molar equivalence is based on Compound 1b).

An example of the present invention includes a process wherein the amount of water used is in a range of from about 1 molar equivalent to about 26 molar equivalents (wherein the molar equivalence is based on Compound 1b).

An example of the present invention includes a process wherein the amount of water used is in a range of from about 1 molar equivalent to about 13 molar equivalents (wherein the molar equivalence is based on Compound 1b).

An example of the present invention includes a process wherein the amount of solvent and the amount of water used in Step 1 are in a ratio, wherein the ratio is in a range of from 6:5 (v/v) to about 11:1 (v/v) solvent:water.

An example of the present invention includes a process wherein the solvent to water ratio used in Step 1 is a ratio of about 11:1 (v/v) solvent:water, or is a ratio of about 9:1 (v/v) solvent:water, or is a ratio of about 9:2 (v/v) solvent:water, or is a ratio of about 8:3 (v/v) solvent:water, or is a ratio of about 8:2 (v/v) solvent:water, or is a ratio of about 7:4 (v/v) solvent:water, or is a ratio of about 6:5 (v/v) solvent:water.

An example of the present invention includes a process wherein the solvent to water ratio used in Step 1 is a ratio of about 9:1 (v/v) solvent:water.

An example of the present invention includes a process wherein the amount of aqueous solvent is in a range of from about 6 ml to about 76 ml per 1 g of Compound 1b.

An example of the present invention includes a process wherein the amount of aqueous solvent is in a range of from about 9 ml to about 11 ml per 1 g of Compound 1b.

An example of the present invention includes a process wherein the amount of aqueous solvent is about 10 ml per 1 g of Compound 1b.

An example of the present invention includes a process wherein the catalytic amount of acid is in a range of from about 0.01 molar equivalents to about 2 molar equivalents (wherein the molar equivalence is based on Compound 1b).

An example of the present invention includes a process wherein the catalytic amount of acid is in a range of from about 0.01 molar equivalents to about 0.15 molar equivalents (wherein the molar equivalence is based on Compound 1b).

An example of the present invention includes a process wherein the catalytic amount of acid is in a range of from about 0.1 molar equivalents to about 0.15 molar equivalents (wherein the molar equivalence is based on Compound 1b).

An example of the present invention includes a process wherein the acid is HCl, wherein Ra in Compound 1a is chloro or, alternatively, HBr, wherein Ra in Compound 1a is bromo.

An example of the present invention includes a process wherein the water and the solvent used in Step 1 are mixed prior to the addition of other reactants, thus forming an aqueous solvent.

An example of the present invention includes a process wherein water and the catalytic amount of acid used in Step 1 are mixed prior to the addition of other reactants, thus forming an aqueous acid.

An example of the present invention includes a process wherein the Compound 1a** and the aqueous solvent are mixed prior to the addition of other reactants.

An example of the present invention includes a process wherein the Compound 1b and the aqueous solvent are mixed prior to the addition of other reactants.

An example of the present invention includes a process wherein Compound 1a**, Compound 1b, the aqueous solvent and the catalytic amount of acid are in a mixture and the reaction mixture is stirred at a temperature of about 40° C., then heated to a temperature of about 65° C.

An example of the present invention includes a process wherein a first portion of about 20% of the total amount of Compound 1b is added to a mixture of Compound 1a** and the aqueous solvent and the resulting reaction mixture is stirred at a temperature of about 40° C.; then, a second portion of about 40% of the total amount of Compound 1b is added and the reaction mixture is stirred at a temperature of about 40° C.; and, a third portion of about 40% of the total amount of Compound 1b is added and the reaction mixture is stirred at a temperature of about 40° C., then heated to a temperature of about 65° C.

An example of the present invention includes a process wherein Compound 1c** is isolated as a free base or as a mono-acid salt.

The presence of water and acid in Step 1 reduces the undesired imine Compounds AA3 and AA4. However, the presence of water in Step 2 may slow the reaction rate and may result in various amounts of the Z-isomer of Compound 78**. Water may be removed in Step 2, such as by azeotropic distillation.

In a preferred embodiment of a one-pot synthesis, the solvent selected for use in Step 2 should be substantially the same solvent as that chosen for use in Step 1.

An example of the present invention includes a process wherein the solvent used in Step 2 of the reaction is selected from isopropanol, 2-methoxy-ethanol, 1-propanol, methanol, ethanol, 1-butanol, THF, 2-Me-THF or acetonitrile.

An example of the present invention includes a process wherein the solvent used in Step 2 is selected from isopropanol, 2-methoxy-ethanol, 1-propanol or acetonitrile.

An example of the present invention includes a process wherein the solvent used in Step 2 is 2-methoxy-ethanol.

An example of the present invention includes a process wherein the Compound 1c is a mono-acid salt or a free base and the Compound 1d is a free-base, mono-acid salt or a bis-acid salt.

An example of the present invention includes a process wherein the Compound 1c is a mono-acid salt and the Compound 1d is a bis-acid salt.

An example of the present invention includes a process wherein the Compound 1c mono-acid salt and Compound 1d bis-acid salt are in about a 1:1 molar equivalent ratio.

An example of the present invention includes a process wherein the base used in Step 2 is present in a stoichiometric amount and, wherein said amount varies upon whether the reaction product is a freebase, a mono-acid salt or as a bis-acid salt of Compound 78.

An example of the present invention includes a process wherein the base used in Step 2 is present in about 2 molar equivalents.

An example of the present invention includes a process wherein the Compound 1c mono-acid salt, the Compound 1d bis-acid salt and the base are in about a 1:1:2 molar equivalent ratio.

An example of the present invention includes a process wherein the base used in Step 2 is NaOH or NaHCO$_3$.

An example of the present invention includes a process wherein Compound 78** is obtained as an acid salt precipitate during azeotropic distillation at a temperature in a range of from about 102° C. to about 115° C. and, wherein the distilled liquid is controlled to an amount of about twice the amount of water initially added.

An example of the present invention includes a process wherein Compound 1c mono-acid salt is reacted with the Compound 1d bis-acid salt and the base at a temperature in a range of from about 106° C. to about 113° C.

An example of the present invention includes a process wherein Compound 78 is obtained as a freebase, a mono-acid salt or as a bis-acid salt.

An example of the present invention includes a process wherein the Compound 78** mono-acid salt is recrystallized from a solvent system selected from 1-propanol and water or isopropanol and water, wherein the solvent is in a ratio with water, and wherein the ratio of solvent:water is about 1:1 (v/v).

An example of the present invention includes a process wherein the recrystallization solvent system is 1-propanol and water, wherein 1-propanol is in a ratio with water, and wherein the ratio of 1-propanol:water is about 1:1 (v/v).

An example of the present invention includes a process wherein the Compound 78** acid salt is a Compound 78* mono-hydrochloric acid salt.

Scheme I illustrates the process of the present invention directed to preparing a Compound 78* mono-hydrochloric acid salt of the formula:

Scheme I

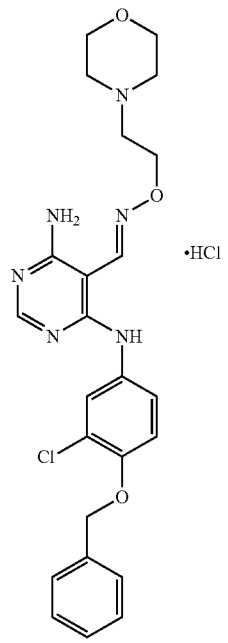

Cpd 78* comprising the steps of:

Step 1. reacting a 4-amino-6-chloro-pyrimidine-5-carbaldehyde Compound 1a, a 4-benzyloxy-3-chloro-phenylamine Compound 1b in an aqueous solvent and a catalytic amount of hydrochloric acid to provide a 4-amino-6-(4-benzyloxy-3-chloro-phenylamino)-pyrimidine-5-carbaldehyde Compound 1c mono-hydrochloric acid salt:

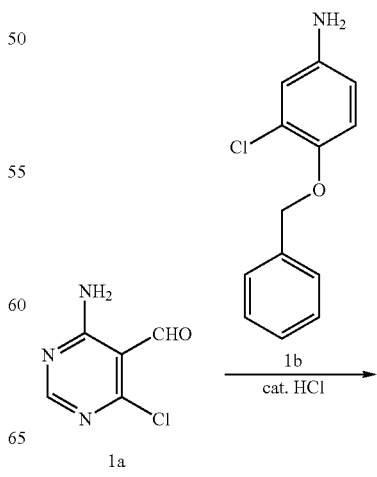

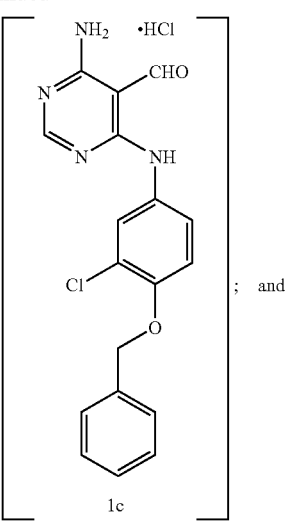

Step 2. reacting the Compound 1c mono-hydrochloric acid salt with a Compound 1d bis-hydrochloric acid salt and a base to provide a Compound 78* mono-hydrochloric acid salt, representative of a compound of Formula (I):

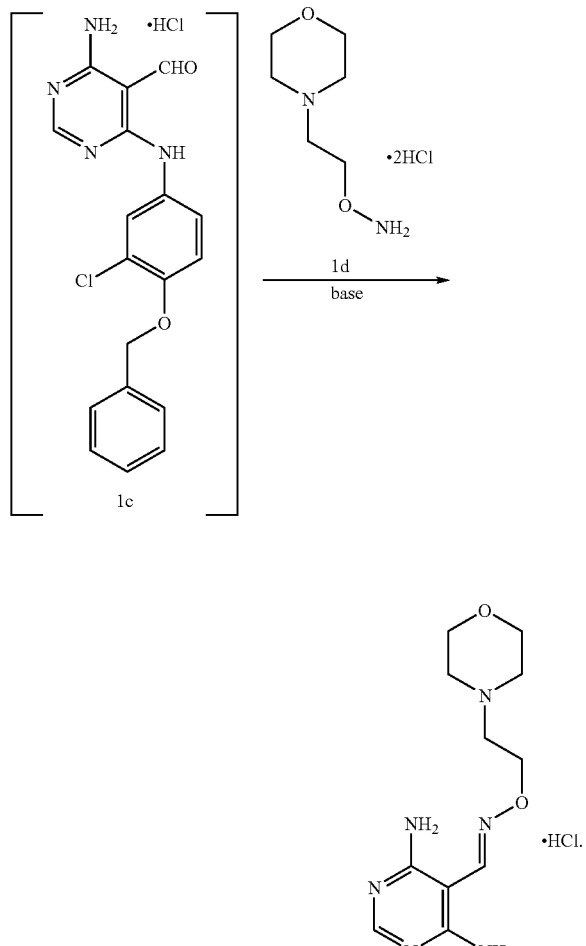

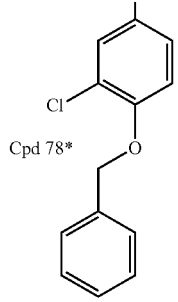

An example of the present invention includes a process wherein a mixture of geometric isomers of Compound 78* may be formed, in particular, a mixture of geometric isomers consisting of a Compound 78* E-isomer and a corresponding Z-isomer.

An example of the present invention includes a process wherein the Compound 78* E-isomer is obtained.

An example of the present invention includes a process wherein one of the solvents used in Step 1 of the reaction is water and the other is optionally selected from isopropanol, 2-methoxy-ethanol, 1-propanol, methanol, ethanol, 1-butanol, THF, 2-Me-THF, toluene or acetonitrile.

An example of the present invention includes a process wherein one of the solvents used in Step 1 is water and the other is optionally selected from isopropanol, 2-methoxy-ethanol, 1-propanol or acetonitrile.

An example of the present invention includes a process wherein the solvent used in Step 1 is water.

An example of the present invention includes a process wherein the solvent used in Step 1 is water and the other is 2-methoxy-ethanol.

An example of the present invention includes a process wherein the amount of water is at least 0.005 molar equivalents (wherein the molar equivalence is based on Compound 1b).

An example of the present invention includes a process wherein the amount of water is in a range of from about 1 molar equivalent to about 99 molar equivalents (wherein the molar equivalence is based on Compound 1b).

An example of the present invention includes a process wherein the amount of water is in a range of from about 1 molar equivalent to about 26 molar equivalents (wherein the molar equivalence is based on Compound 1b).

An example of the present invention includes a process wherein the amount of water is in a range of from about 1 molar equivalent to about 13 molar equivalents (wherein the molar equivalence is based on Compound 1b).

An example of the present invention includes a process wherein the amount of solvent and the amount of water used in Step 1 are in a ratio, wherein the ratio is in a range of from 6:5 (v/v) to about 11:1 (v/v) solvent:water.

An example of the present invention includes a process wherein the solvent to water ratio used in Step 1 is a ratio of about 11:1 (v/v) solvent:water, or is a ratio of about 9:1 (v/v) solvent:water, or is a ratio of about 9:2 (v/v) solvent:water, or is a ratio of about 8:3 (v/v) solvent:water, is a ratio of about 8:2 (v/v) solvent:water, or is a ratio of about 7:4 (v/v) solvent:water, or is a ratio of about 6:5 (v/v) solvent:water.

An example of the present invention includes a process wherein the solvent to water ratio used in Step 1 is a ratio of about 9:1 (v/v) solvent:water.

An example of the present invention includes a process wherein the amount of aqueous solvent is in a range of from about 6 ml to about 76 ml per 1 g of Compound 1b.

An example of the present invention includes a process wherein the amount of aqueous solvent is in a range of from about 9 ml to about 11 ml per 1 g of Compound 1b.

An example of the present invention includes a process wherein the amount of aqueous solvent is about 10 ml per 1 g of Compound 1b.

An example of the present invention includes a process wherein the catalytic amount of acid is in a range of from about 0.01 molar equivalents to about 2 molar equivalents (wherein the molar equivalence is based on Compound 1b).

An example of the present invention includes a process wherein the catalytic amount of acid is in a range of from about 0.01 molar equivalents to about 0.15 molar equivalents (wherein the molar equivalence is based on Compound 1b).

An example of the present invention includes a process wherein the catalytic amount of acid is in a range of from about 0.1 molar equivalents to about 0.15 molar equivalents (wherein the molar equivalence is based on Compound 1b).

An example of the present invention includes a process wherein the water and the solvent used in Step 1 are mixed prior to the addition of other reactants, thus forming an aqueous solvent.

An example of the present invention includes a process wherein water and the catalytic amount of acid used in Step 1 are mixed prior to the addition of other reactants, thus forming an aqueous acid.

An example of the present invention includes a process wherein the Compound 1a and the aqueous solvent are mixed prior to the addition of other reactants.

An example of the present invention includes a process wherein the Compound 1b and the aqueous solvent are mixed prior to the addition of other reactants.

An example of the present invention includes a process wherein Compound 1a, Compound 1b, the aqueous solvent and the catalytic amount of acid are in a mixture and the reaction mixture is stirred at a temperature of about 40° C., then heated to a temperature of about 65° C.

An example of the present invention includes a process wherein a first portion of about 20% of the total amount of Compound 1b is added to a mixture of Compound 1a and the aqueous solvent and the resulting reaction mixture is stirred at a temperature of about 40° C.; then, a second portion of about 40% of the total amount of Compound 1b is added and the reaction mixture is stirred at a temperature of about 40° C.; and, a third portion of about 40% of the total amount of Compound 1b is added and the reaction mixture is stirred at a temperature of about 40° C., then heated to a temperature of about 65° C.

An example of the present invention includes a process wherein Compound 1c is isolated as a free base or as a mono-hydrochloric acid salt.

The presence of water in Step 1 reduces the formation of the undesired imine Compounds AA3 and AA4. However, the presence of water in Step 2 may slow the reaction rate and may result in various amounts of the Z-isomer of Compound 78*. Water may be removed in Step 2, such as by azeotropic distillation.

In a preferred embodiment of a one-pot synthesis, the solvent selected for use in Step 2 should be substantially the same solvent as that chosen for use in Step 1.

An example of the present invention includes a process wherein the solvent used in Step 2 of the reaction is selected from isopropanol, 2-methoxy-ethanol, 1-propanol, methanol, ethanol, 1-butanol, THF, 2-Me-THF or acetonitrile.

An example of the present invention includes a process wherein the solvent used in Step 2 is selected from isopropanol, 2-methoxy-ethanol, 1-propanol or acetonitrile.

An example of the present invention includes a process wherein the solvent used in Step 2 is 2-methoxy-ethanol.

An example of the present invention includes a process wherein Compound 1c is a freebase or a mono-hydrochloric acid salt and the Compound 1d is a freebase, a mono-hydrochloric acid salt or bis-hydrochloric acid salt.

An example of the present invention includes a process wherein Compound 1c is a mono-hydrochloric acid salt and the Compound 1d is a bis-hydrochloric acid salt.

An example of the present invention includes a process wherein the Compound 1c mono-hydrochloric acid salt and the Compound 1d bis-hydrochloric acid salt are in about a 1:1 molar equivalent ratio.

An example of the present invention includes a process wherein the base used in Step 2 is present in a stoichiometric amount and, wherein said amount varies upon whether the reaction product is a freebase (Compound 78), a mono-hydrochloric acid salt (Compound 78*) or as a bis-hydrochloric acid salt of Compound 78 (Compound AA5).

An example of the present invention includes a process wherein the base used in Step 2 is present in about 2 molar equivalents.

An example of the present invention includes a process wherein the Compound 1c mono-hydrochloric acid salt, the Compound 1d bis-hydrochloric acid salt and the base are in about a 1:1:2 molar equivalent ratio.

An example of the present invention includes a process wherein the base used in Step 2 is NaOH or NaHCO$_3$.

An example of the present invention includes a process wherein Compound 78* is obtained as a mono-hydrochloric acid salt precipitate during azeotropic distillation at a temperature in a range of from about 102° C. to about 115° C. and, wherein the distilled liquid is controlled to an amount of about twice the amount of water initially added.

An example of the present invention includes a process wherein the Compound 1c mono-hydrochloric acid salt is reacted with the Compound 1d bis-hydrochloric acid salt and the base at a temperature in a range of from about 106° C. to about 113° C.

An example of the present invention includes a process wherein Compound 78 is obtained as a freebase, a mono-hydrochloric acid salt or as a bis-hydrochloric acid salt.

An example of the present invention includes a process wherein the Compound 78* mono-hydrochloric acid salt is recrystallized from a solvent system selected from 1-propanol and water or isopropanol and water, wherein the solvent is in a ratio with water, and wherein the ratio of solvent:water is about 1:1 (v/v).

An example of the present invention includes a process wherein the recrystallization solvent system is 1-propanol and water, wherein 1-propanol is in a ratio with water, and wherein the ratio of 1-propanol:water is about 1:1 (v/v).

The present invention is also directed to a process for preparing compounds described in U.S. patent application Ser. No. 11/609,450, filed Dec. 12, 2006.

An example of the present invention includes a process for preparing compounds of Formula (I) described in U.S. patent application Ser. No. 11/609,450 selected from the group consisting of:

Cpd Names 1 (5E)-4-amino-6-(3-chloro-4-fluoro-phenylamino)-pyrimidine-5-carbaldehyde O-methyl-oxime, 2 (5E)-4-amino-6-[1-(3-fluoro-benzyl)-1H-indazol-5-ylamino]-pyrimidine-5-carbaldehyde O-methyl-oxime, 3 (5E)-4-amino-6-(3-chloro-4-fluoro-benzylamino)-pyrimidine-5-carbaldehyde O-methyl-oxime,
4 (5E)-4-amino-6-[3-chloro-4-(3-fluoro-benzyloxy)-phenylamino]-pyrimidine-5-carbaldehyde O-methyl-oxime,
5 (5E)-4-amino-6-[2-(3-fluoro-benzyl)-2H-indazol-5-ylamino]-pyrimidine-5-carbaldehyde O-methyl-oxime,
6 (5E)-4-amino-6-[1-(3-fluoro-benzyl)-1H-indazol-5-ylamino]-pyrimidine-5-carbaldehyde O-(2-morpholin-4-yl-2-oxo-ethyl)-oxime,
7 (5E)-4-amino-6-(3-methoxy-4-phenoxy-phenylamino)-pyrimidine-5-carbaldehyde O-methyl-oxime,
8 (5E)-4-amino-6-(3-methoxy-4-phenoxy-phenylamino)-pyrimidine-5-carbaldehyde O-(2-morpholin-4-yl-2-oxo-ethyl)-oxime,
9 (5E)-4-amino-6-(4-benzyloxy-3-chloro-phenylamino)-pyrimidine-5-carbaldehyde O-methyl-oxime,
10 (5E)-4-amino-6-[1-(3-fluoro-benzyl)-1H-indazol-5-ylamino]-pyrimidine-5-carbaldehyde O-ethyl-oxime,
11 (5E)-4-amino-6-[1-(3-fluoro-benzyl)-1H-indazol-5-ylamino]-pyrimidine-5-carbaldehyde O-allyl-oxime,
12 (5E)-4-amino-6-[1-(3-fluoro-benzyl)-1H-indazol-5-ylamino]-pyrimidine-5-carbaldehyde O-tert-butyl-oxime,
13 (5E)-4-amino-6-[3-methyl-4-(pyridin-3-yloxy)-phenylamino]-pyrimidine-5-carbaldehyde O-methyl-oxime,
14 (5E)-4-amino-6-[(1R)-1-phenyl-ethylamino]-pyrimidine-5-carbaldehyde O-ethyl-oxime,
16 (5E)-4-amino-6-[(1S)-1-phenyl-ethylamino]-pyrimidine-5-carbaldehyde O-ethyl-oxime,
17 (5E)-4-amino-6-(1H-indol-5-ylamino)-pyrimidine-5-carbaldehyde O-ethyl-oxime,
18 (5E)-4-amino-6-[3-chloro-4-(3-fluoro-benzyloxy)-phenylamino]-pyrimidine-5-carbaldehyde O-ethyl-oxime,
19 (5E)-4-amino-6-[1-(3-fluoro-benzyl)-1H-indazol-5-ylamino]-pyrimidine-5-carbaldehyde O-(2-morpholin-4-yl-ethyl)-oxime,
20 (5E)-4-amino-6-(indan-5-ylamino)-pyrimidine-5-carbaldehyde O-methyl-oxime,
21 (5E)-4-amino-6-(4-difluoromethoxy-phenylamino)-pyrimidine-5-carbaldehyde O-methyl-oxime,
22 (5E)-4-amino-6-(1H-indazol-5-ylamino)-pyrimidine-5-carbaldehyde O-methyl-oxime,
23 (5E)-4-amino-6-(benzo[1,3]dioxol-5-ylamino)-pyrimidine-5-carbaldehyde O-methyl-oxime,
24 (5E)-4-amino-6-(4-phenoxy-phenylamino)-pyrimidine-5-carbaldehyde O-methyl-oxime,
25 (5E)-4-amino-6-(4-benzyloxy-phenylamino)-pyrimidine-5-carbaldehyde O-methyl-oxime,
26 (5E)-4-amino-6-(4-sec-butyl-phenylamino)-pyrimidine-5-carbaldehyde O-methyl-oxime,
27 (5E)-4-amino-6-(4-tert-butyl-phenylamino)-pyrimidine-5-carbaldehyde O-methyl-oxime,
28 (5E)-4-amino-6-(3-benzyloxy-phenylamino)-pyrimidine-5-carbaldehyde O-methyl-oxime,
29 (5E)-4-amino-6-[3-methyl-4-(6-methyl-pyridin-3-yloxy)-phenylamino]-pyrimidine-5-carbaldehyde O-methyl-oxime,
30 (5E)-4-amino-6-[1-(3-fluoro-benzyl)-1H-indazol-5-ylamino]-pyrimidine-5-carbaldehyde O-isobutyl-oxime,
31 (5E)-4-amino-6-[1-(3-fluoro-benzyl)-1H-indazol-5-ylamino]-pyrimidine-5-carbaldehyde O-(2-phenoxy-ethyl)-oxime,
32 (5E)-4-amino-6-[3-chloro-4-(pyridin-2-ylmethoxy)-phenylamino]-pyrimidine-5-carbaldehyde O-methyl-oxime,
33 (5E)-4-amino-6-[1-(3-fluoro-benzyl)-1H-indol-5-ylamino]-pyrimidine-5-carbaldehyde O-ethyl-oxime,
34 (5E)-4-amino-6-[1-(3-fluoro-benzyl)-1H-indol-5-ylamino]-pyrimidine-5-carbaldehyde O-methyl-oxime,
35 (5E)-4-amino-6-[2,2-difluoro-2-(6-methyl-pyridin-2-yl)-ethylamino]-pyrimidine-5-carbaldehyde O-methyl-oxime,
36 (5E)-4-amino-6-(3-bromo-phenylamino)-pyrimidine-5-carbaldehyde O-methyl-oxime,
37 (5E)-4-amino-6-(4-benzyloxy-3-chloro-phenylamino)-pyrimidine-5-carbaldehyde O-ethyl-oxime,
38 (5E)-4-amino-6-[3-chloro-4-(pyridin-3-yloxy)-phenylamino]-pyrimidine-5-carbaldehyde O-methyl-oxime,
39 4-[3-chloro-4-(3-fluoro-benzyloxy)-phenylamino]-6-methylamino-pyrimidine-5-carbaldehyde O-methyl-oxime,
40 (5E)-4-ethylamino-6-[1-(3-fluoro-benzyl)-1H-indazol-5-ylamino]-pyrimidine-5-carbaldehyde O-methyl-oxime,
41 (5E)-4-ethylamino-6-[1-(3-fluoro-benzyl)-1H-indazol-5-ylamino]-pyrimidine-5-carbaldehyde O-ethyl-oxime,
42 (5E)-4-[3-chloro-4-(3-fluoro-benzyloxy)-phenylamino]-6-ethylamino-pyrimidine-5-carbaldehyde O-methyl-oxime,
43 (5E)-4-[3-chloro-4-(3-fluoro-benzyloxy)-phenylamino]-6-ethylamino-pyrimidine-5-carbaldehyde O-ethyl-oxime,
44 (5E)-4-amino-6-[1-(3-fluoro-benzyl)-1H-indazol-5-ylamino]-pyrimidine-5-carbaldehyde O-(4-methoxy-benzyl)-oxime,
45 (5E)-4-amino-6-[1-(3-fluoro-benzyl)-1H-indazol-5-ylamino]-pyrimidine-5-carbaldehyde O-(2-methoxy-benzyl)-oxime,
46 (5E)-4-amino-6-[1-(3-fluoro-benzyl)-1H-indazol-5-ylamino]-pyrimidine-5-carbaldehyde O-benzyl-oxime,
47 (5E)-4-amino-6-[1-(3-fluoro-benzyl)-1H-indazol-5-ylamino]-pyrimidine-5-carbaldehyde O-isopropyl-oxime,
48 (5E)-4-amino-6-(1-benzyl-1H-indazol-5-ylamino)-pyrimidine-5-carbaldehyde O-methyl-oxime,
49 (5E)-4-amino-6-(1-benzyl-1H-indazol-5-ylamino)-pyrimidine-5-carbaldehyde O-ethyl-oxime,
50 3-{5-[6-amino-(5E)-5-(methoxyimino-methyl)-pyrimidin-4-ylamino]-indazol-1-ylmethyl}-benzonitrile,
51 3-{5-[6-amino-(5E)-5-(ethoxyimino-methyl)-pyrimidin-4-ylamino]-indazol-1-ylmethyl}-benzonitrile,
52 (5E)-4-amino-6-(2-benzyl-2H-indazol-5-ylamino)-pyrimidine-5-carbaldehyde O-ethyl-oxime,
53 (5E)-4-[1-(3-fluoro-benzyl)-1H-indazol-5-ylamino]-6-methylamino-pyrimidine-5-carbaldehyde O-methyl-oxime,
54 (5E)-4-amino-6-[1-(3-chloro-benzyl)-1H-indazol-5-ylamino]-pyrimidine-5-carbaldehyde O-methyl-oxime,
55 (5E)-4-amino-6-[1-(3-chloro-benzyl)-1H-indazol-5-ylamino]-pyrimidine-5-carbaldehyde O-ethyl-oxime,
56 (5E)-4-amino-6-[1-(3-methoxy-benzyl)-1H-indazol-5-ylamino]-pyrimidine-5-carbaldehyde O-methyl-oxime,
57 (5E)-4-amino-6-[1-(3-methoxy-benzyl)-1H-indazol-5-ylamino]-pyrimidine-5-carbaldehyde O-ethyl-oxime,
58 (5E)-4-amino-6-[2-(3-fluoro-benzyl)-1H-benzoimidazol-5-ylamino]-pyrimidine-5-carbaldehyde O-ethyl-oxime,
59 (5E)-4-amino-6-(3-chloro-phenylamino)-pyrimidine-5-carbaldehyde O-methyl-oxime,
60 (5E)-4-amino-6-[2-(3-fluoro-benzyl)-1H-benzoimidazol-5-ylamino]-pyrimidine-5-carbaldehyde O-methyl-oxime,
61 (5E)-4-amino-6-[4-(3-fluoro-benzyloxy)-3-methoxy-phenylamino]-pyrimidine-5-carbaldehyde O-methyl-oxime,
62 (5E)-4-amino-6-[4-(3-fluoro-benzyloxy)-3-methoxy-phenylamino]-pyrimidine-5-carbaldehyde O-ethyl-oxime,
63 (5E)-4-amino-6-(3-chloro-4-methoxy-phenylamino)-pyrimidine-5-carbaldehyde O-methyl-oxime,
64 (5E)-4-amino-6-(3-chloro-4-morpholin-4-yl-phenylamino)-pyrimidine-5-carbaldehyde O-methyl-oxime, 65 (5E)-4-amino-6-[1-(3-fluoro-benzyl)-1H-indazol-5-ylamino]-pyrimidine-5-carbaldehyde O-phenyl-oxime,
66 (5E)-4-amino-6-[1-(4-fluoro-benzyl)-1H-indazol-5-ylamino]-pyrimidine-5-carbaldehyde O-methyl-oxime,
67 (5E)-4-amino-6-[1-(4-fluoro-benzyl)-1H-indazol-5-ylamino]-pyrimidine-5-carbaldehyde O-ethyl-oxime,
68 (5E)-4-amino-6-[1-(3-fluoro-benzyl)-1H-indazol-5-ylamino]-pyrimidine-5-carbaldehyde O-(2-methoxy-ethyl)-oxime,
70 (5E)-4-amino-6-[1-(3-fluoro-benzyl)-1H-indazol-5-ylamino]-pyrimidine-5-carbaldehyde O-(3-dimethylamino-propyl)-oxime,
71 (5E)-4-amino-6-(4-benzyloxy-3-chloro-phenylamino)-pyrimidine-5-carbaldehyde O-(2-methoxy-ethyl)-oxime,
72 (5E)-4-amino-6-[2-(3-fluoro-phenyl)-benzofuran-5-ylamino]-pyrimidine-5-carbaldehyde O-methyl-oxime,
73 (5E)-4-amino-6-(2-benzyl-benzofuran-5-ylamino)-pyrimidine-5-carbaldehyde O-methyl-oxime,
74 (5E)-4-amino-6-[1-(3-fluoro-benzyl)-2,3-dihydro-1H-indol-5-ylamino]-pyrimidine-5-carbaldehyde O-methyl-oxime,
75 (5E)-4-amino-6-[3-chloro-4-(3-fluoro-benzyloxy)-phenylamino]-pyrimidine-5-carbaldehyde O-(3-hydroxy-propyl)-oxime,
76 (5E)-4-amino-6-(4-benzyloxy-3-chloro-phenylamino)-pyrimidine-5-carbaldehyde O-(3-hydroxy-propyl)-oxime,
77 (5E)-4-amino-6-(4-benzyloxy-3-chloro-phenylamino)-pyrimidine-5-carbaldehyde oxime,
78 (5E)-4-amino-6-(4-benzyloxy-3-chloro-phenylamino)-pyrimidine-5-carbaldehyde O-(2-morpholin-4-yl-ethyl)-oxime,
78* (5E)-4-amino-6-(4-benzyloxy-3-chloro-phenylamino)-pyrimidine-5-carbaldehyde O-(2-morpholin-4-yl-ethyl)-oxime mono-hydrochloride salt,
78** (5E)-4-amino-6-(4-benzyloxy-3-chloro-phenylamino)-pyrimidine-5-carbaldehyde O-(2-morpholin-4-yl-ethyl)-oxime bis-hydrochloride salt,
79 (5E)-4-amino-6-[3-chloro-4-(3-fluoro-benzyloxy)-phenylamino]-pyrimidine-5-carbaldehyde oxime,
80 (5E)-4-amino-6-(4-chloro-2-fluoro-phenylamino)-pyrimidine-5-carbaldehyde O-methyl-oxime,
82 (5E)-4-amino-6-(4-bromo-2-fluoro-phenylamino)-pyrimidine-5-carbaldehyde O-methyl-oxime,
84 (5E)-4-amino-6-[1-(3-fluoro-benzyl)-1H-indazol-5-ylamino]-pyrimidine-5-carbaldehyde oxime,
85 (5E)-4-amino-6-[1-(3-fluoro-benzyl)-1H-indazol-5-ylamino]-pyrimidine-5-carbaldehyde O-(3-hydroxy-propyl)-oxime,
86 (5E)-4-(4-bromo-2-fluoro-phenylamino)-6-methoxyamino-pyrimidine-5-carbaldehyde O-methyl-oxime,
87 (5E)-4-amino-6-[1-(3-fluoro-benzyl)-1H-indazol-5-ylamino]-pyrimidine-5-carbaldehyde O-(3-morpholin-4-yl-propyl)-oxime,
88 (5E)-4-amino-6-[1-(3-fluoro-benzyl)-1H-indol-5-ylamino]-pyrimidine-5-carbaldehyde oxime,
89 (5E)-4-amino-6-(4-chloro-2-fluoro-5-hydroxy-phenylamino)-pyrimidine-5-carbaldehyde O-methyl-oxime,
91 (5E)-4-amino-6-[1-(3-fluoro-benzyl)-1H-indol-5-ylamino]-pyrimidine-5-carbaldehyde O-(3-hydroxy-propyl)-oxime,
92 (5E)-4-amino-6-[1-(3-fluoro-benzyl)-1H-indazol-5-ylamino]-pyrimidine-5-carbaldehyde O-(3-piperidin-1-yl-propyl)-oxime,
93 (5E)-4-amino-6-[3-chloro-4-(3-fluoro-benzyloxy)-phenylamino]-pyrimidine-5-carbaldehyde O-(2-morpholin-4-yl-ethyl)-oxime,
94 (5E)-4-amino-6-[3-chloro-4-(3-fluoro-benzyloxy)-phenylamino]-pyrimidine-5-carbaldehyde O-(2-piperidin-1-yl-ethyl)-oxime,
95 (5E)-4-amino-6-(4-benzyloxy-3-chloro-phenylamino)-pyrimidine-5-carbaldehyde O-(2-piperidin-1-yl-ethyl)-oxime,
96 (5E)-4-amino-6-[1-(3-fluoro-benzyl)-1H-indazol-5-ylamino]-pyrimidine-5-carbaldehyde O-(2-piperidin-1-yl-ethyl)-oxime,
97 (5E)-4-amino-6-[3-chloro-4-(3,5-difluoro-benzyloxy)-phenylamino]-pyrimidine-5-carbaldehyde O-methyl-oxime,
98 (5E)-4-amino-6-[3-chloro-4-(3,5-difluoro-benzyloxy)-phenylamino]-pyrimidine-5-carbaldehyde oxime,
99 (5E)-4-amino-6-[3-chloro-4-(3,5-difluoro-benzyloxy)-phenylamino]-pyrimidine-5-carbaldehyde O-(2-morpholin-4-yl-ethyl)-oxime,
100 (5E)-4-amino-6-[(1S)-1-phenyl-ethylamino]-pyrimidine-5-carbaldehyde oxime,
101 (5E)-4-amino-6-[1-(3-fluoro-benzyl)-1H-indol-5-ylamino]-pyrimidine-5-carbaldehyde O-(2-morpholin-4-yl-ethyl)-oxime,
102 (5E)-4-amino-6-[1-(3-fluoro-benzyl)-1H-indol-5-ylamino]-pyrimidine-5-carbaldehyde O-(2-piperidin-1-yl-ethyl)-oxime,
103 (5E)-4-amino-6-[(1S)-1-phenyl-ethylamino]-pyrimidine-5-carbaldehyde O-(2-morpholin-4-yl-ethyl)-oxime,
104 N-{4-[6-amino-(5E)-5-(methoxyimino-methyl)-pyrimidin-4-ylamino]-phenyl}-benzamide,
105 N-{4-[6-amino-(5E)-5-(hydroxyimino-methyl)-pyrimidin-4-ylamino]-phenyl}-benzamide,
106 (5E)-4-amino-6-[(1S)-1-phenyl-ethylamino]-pyrimidine-5-carbaldehyde O-(2-piperidin-1-yl-ethyl)-oxime,
107 N-(4-{6-amino-(5E)-5-[(2-morpholin-4-yl-ethoxyimino)-methyl]-pyrimidin-4-ylamino}-phenyl)-benzamide,
108 (5E)-4-amino-6-(3-chloro-4-fluoro-phenylamino)-pyrimidine-5-carbaldehyde O-(2-morpholin-4-yl-ethyl)-oxime,
109 (5E)-4-amino-6-(4-phenoxy-phenylamino)-pyrimidine-5-carbaldehyde O-(2-morpholin-4-yl-ethyl)-oxime,
110 N-{5-[6-amino-(5E)-5-(methoxyimino-methyl)-pyrimidin-4-ylamino]-pyrimidin-2-yl}-benzamide,
111 (5E)-4-amino-6-(4-phenoxy-phenylamino)-pyrimidine-5-carbaldehyde oxime,
112 (5E)-4-amino-6-(4-benzyloxy-3-chloro-phenylamino)-pyrimidine-5-carbaldehyde O-(3-morpholin-4-yl-propyl)-oxime,
113 methanesulfonic acid (5E)-3-[4-amino-6-(4-benzyloxy-3-chloro-phenylamino)-pyrimidin-5-ylmethyleneaminooxy]-propyl ester,
114 (5E)-4-amino-6-(4-benzyloxy-3-chloro-phenylamino)-pyrimidine-5-carbaldehyde O-pyridin-2-ylmethyl-oxime,
115 (5E)-4-amino-6-(4-benzyloxy-3-chloro-phenylamino)-pyrimidine-5-carbaldehyde O-[3-(2-methoxy-ethylamino)-propyl]-oxime,
116 (5E)-4-amino-6-(4-benzyloxy-3-chloro-phenylamino)-pyrimidine-5-carbaldehyde O-[3-(4-hydroxy-piperidin-1-yl)-propyl]-oxime,
117 (5E)-4-[4-amino-6-(4-benzyloxy-3-chloro-phenylamino)-pyrimidin-5-ylmethyleneaminooxymethyl]-piperidine-1-carboxylic acid tert-butyl ester,
118 4-amino-6-(4-benzyloxy-3-chloro-phenylamino)-pyrimidine-5-carbonitrile,
119 N-benzo[1,3]dioxol-5-ylmethyl-5-[(benzo[1,3]dioxol-5-ylmethylimino)-methyl]-pyrimidine-4,6-diamine, 120 4-amino-6-(4-methoxy-phenylamino)-pyrimidine-5-carbaldehyde O-methyl-oxime,
121 4-amino-6-[(benzo[1,3]dioxol-5-ylmethyl)-amino]-pyrimidine-5-carbaldehyde O-methyl-oxime,
122 4-amino-6-(3,4-dimethoxy-benzylamino)-pyrimidine-5-carbaldehyde O-methyl-oxime,
123 4-amino-6-(4-phenoxy-benzylamino)-pyrimidine-5-carbaldehyde O-methyl-oxime,
124 4-amino-6-(indan-1-ylamino)-pyrimidine-5-carbaldehyde O-methyl-oxime,
125 4-amino-6-(1,2,3,4-tetrahydro-naphthalen-1-ylamino)-pyrimidine-5-carbaldehyde O-methyl-oxime,
126 4-amino-6-[1-(4-chloro-phenyl)-ethylamino]-pyrimidine-5-carbaldehyde O-methyl-oxime,
127 4-amino-6-[1-(4-methoxy-phenyl)-ethylamino]-pyrimidine-5-carbaldehyde O-methyl-oxime,
128 4-amino-6-(6-phenoxy-pyridin-3-ylamino)-pyrimidine-5-carbaldehyde O-methyl-oxime,
129 4-amino-6-(6-morpholin-4-yl-pyridin-3-ylamino)-pyrimidine-5-carbaldehyde O-methyl-oxime,
130 4-amino-6-(1,4-dioxo-1,2,3,4-tetrahydro-phthalazin-5-ylamino)-pyrimidine-5-carbaldehyde O-methyl-oxime,
131 4-amino-6-(2-fluoro-5-methyl-phenylamino)-pyrimidine-5-carbaldehyde O-methyl-oxime,
132 4-amino-6-(2,4,6-trimethyl-phenylamino)-pyrimidine-5-carbaldehyde O-methyl-oxime,
133 4-amino-6-(3-chloro-2-methyl-phenylamino)-pyrimidine-5-carbaldehyde O-methyl-oxime,
134 4-amino-6-(3-methylsulfanyl-phenylamino)-pyrimidine-5-carbaldehyde O-methyl-oxime,
136 4-amino-6-(3,5-dimethyl-phenylamino)-pyrimidine-5-carbaldehyde O-methyl-oxime,
137 N-{4-[6-amino-5-(methoxyimino-methyl)-pyrimidin-4-ylamino]-phenyl}-acetamide,
138 4-amino-6-phenylamino-pyrimidine-5-carbaldehyde O-methyl-oxime,
139 4-amino-6-(4-morpholin-4-yl-phenylamino)-pyrimidine-5-carbaldehyde O-methyl-oxime,
140 4-amino-6-o-tolylamino-pyrimidine-5-carbaldehyde O-methyl-oxime,
141 4-amino-6-(3,4-difluoro-phenylamino)-pyrimidine-5-carbaldehyde O-methyl-oxime,
142 4-amino-6-(3-fluoro-4-methyl-phenylamino)-pyrimidine-5-carbaldehyde O-methyl-oxime,
143 4-amino-6-(3,4-dichloro-phenylamino)-pyrimidine-5-carbaldehyde O-methyl-oxime,
144 4-amino-6-(3-chloro-4-methyl-phenylamino)-pyrimidine-5-carbaldehyde O-methyl-oxime,
145 4-amino-6-[5-chloro-2-methyl-4-(2-oxo-2-phenyl-ethyl)-phenylamino]-pyrimidine-5-carbaldehyde O-methyl-oxime,
146 4-amino-6-(3-ethyl-phenylamino)-pyrimidine-5-carbaldehyde O-methyl-oxime,
147 4-amino-6-(4-isopropyl-phenylamino)-pyrimidine-5-carbaldehyde O-methyl-oxime,
148 4-amino-6-(1H-indol-5-ylamino)-pyrimidine-5-carbaldehyde O-methyl-oxime,
149 4-amino-6-(3-trifluoromethyl-phenylamino)-pyrimidine-5-carbaldehyde O-methyl-oxime,
150 4-amino-6-m-tolylamino-pyrimidine-5-carbaldehyde O-methyl-oxime,
151 4-amino-6-(4-chloro-phenylamino)-pyrimidine-5-carbaldehyde O-methyl-oxime,
152 4-amino-6-(4-chloro-2-methyl-phenylamino)-pyrimidine-5-carbaldehyde O-methyl-oxime,
153 4-amino-6-(4-phenylamino-phenylamino)-pyrimidine-5-carbaldehyde O-methyl-oxime,
154 4-amino-6-(4-diethylamino-phenylamino)-pyrimidine-5-carbaldehyde O-methyl-oxime,
157 4-(4-acetyl-phenylamino)-6-amino-pyrimidine-5-carbaldehyde O-methyl-oxime,
159 {4-[6-amino-5-(methoxyimino-methyl)-pyrimidin-4-ylamino]-phenyl}-acetonitrile,
160 4-amino-6-(2-methoxy-4-phenylamino-phenylamino)-pyrimidine-5-carbaldehyde O-methyl-oxime,
161 N-{4-[6-amino-5-(methoxyimino-methyl)-pyrimidin-4-ylamino]-3-methoxy-phenyl}-acetamide,
162 4-amino-6-(4-cyclohexyl-phenylamino)-pyrimidine-5-carbaldehyde O-methyl-oxime,
163 4-amino-6-(naphthalen-1-ylamino)-pyrimidine-5-carbaldehyde O-methyl-oxime,
164 4-amino-6-(4-chloro-naphthalen-1-ylamino)-pyrimidine-5-carbaldehyde O-methyl-oxime,
165 4-amino-6-(2,4-difluoro-phenylamino)-pyrimidine-5-carbaldehyde O-methyl-oxime,
166 4-amino-6-(2-methylsulfanyl-phenylamino)-pyrimidine-5-carbaldehyde O-methyl-oxime,
167 4-amino-6-(3-fluoro-phenylamino)-pyrimidine-5-carbaldehyde O-methyl-oxime,
168 4-amino-6-(3,5-dichloro-phenylamino)-pyrimidine-5-carbaldehyde O-methyl-oxime,
169 4-amino-6-(3,5-dichloro-phenylamino)-pyrimidine-5-carbaldehyde O-methyl-oxime,
170 4-amino-6-(5-chloro-2-methoxy-phenylamino)-pyrimidine-5-carbaldehyde O-methyl-oxime,
171 4-amino-6-(5-chloro-2-methyl-phenylamino)-pyrimidine-5-carbaldehyde O-methyl-oxime,
172 4-amino-6-(4-fluoro-phenylamino)-pyrimidine-5-carbaldehyde O-methyl-oxime,
173 4-amino-6-(biphenyl-4-ylamino)-pyrimidine-5-carbaldehyde O-methyl-oxime,
174 4-amino-6-(4-methylsulfanyl-phenylamino)-pyrimidine-5-carbaldehyde O-methyl-oxime,
175 4-amino-6-(3,5-dimethoxy-phenylamino)-pyrimidine-5-carbaldehyde O-methyl-oxime,
176 4-amino-6-(3,4,5-trimethoxy-phenylamino)-pyrimidine-5-carbaldehyde O-methyl-oxime,
177 4-amino-6-(3,4-dimethoxy-phenylamino)-pyrimidine-5-carbaldehyde O-methyl-oxime,
178 4-amino-6-(5,6,7,8-tetrahydro-naphthalen-1-ylamino)-pyrimidine-5-carbaldehyde O-methyl-oxime,
179 4-[6-amino-5-(methoxyimino-methyl)-pyrimidin-4-ylamino]-N-pyrimidin-2-yl-benzenesulfonamide,
182 4-amino-6-(4-ethyl-phenylamino)-pyrimidine-5-carbaldehyde O-methyl-oxime,
183 4-[6-amino-5-(methoxyimino-methyl)-pyrimidin-4-ylamino]-N-(3,5-dimethyl-pyrazin-2-yl)-benzenesulfonamide,
184 4-amino-6-(2-methyl-benzothiazol-5-ylamino)-pyrimidine-5-carbaldehyde O-methyl-oxime,
185 4-amino-6-[4-(4-methoxy-phenylamino)-phenylamino]-pyrimidine-5-carbaldehyde O-methyl-oxime,
186 4-amino-6-(4-dimethylamino-phenylamino)-pyrimidine-5-carbaldehyde O-methyl-oxime,
187 4-[6-amino-5-(methoxyimino-methyl)-pyrimidin-4-ylamino]-N-(2-diethylamino-ethyl)-benzamide,
189 4-amino-6-(indan-4-ylamino)-pyrimidine-5-carbaldehyde O-methyl-oxime,
190 4-amino-6-(4'-chloro-biphenyl-4-ylamino)-pyrimidine-5-carbaldehyde O-methyl-oxime,
191 4-amino-6-[6-(4-fluoro-phenoxy)-pyridin-3-ylamino]-pyrimidine-5-carbaldehyde O-methyl-oxime, and
193 N-(4-benzyloxy-3-chloro-phenyl)-5-[5-(2-morpholin-4-yl-ethyl)-[1,3,4]oxadiazol-2-yl]-pyrimidine-4,6-diamine.

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term have an indicated formula. The particular formula provided is not intended to limit the scope of the invention, but is provided as an illustration of the term. The scope of the per se definition of the term is intended to include the plurality of variations expected to be included by one of ordinary skill in the art. Chemical terms are to be read from right to left, wherein the right-most group is attached to the core molecule and the left-most group is the terminal group. The formula(s) illustrating a term are to be read from left to right, wherein the left-most group is attached to the core molecule, as indicated by the dash, and the right-most group is the terminal group.

The term "$C_{1-8}$alkyl" means a saturated aliphatic branched or straight-chain hydrocarbon radical or linking group having from 1 up to 8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule via a terminal carbon atom or via a carbon atom within the chain. Similarly, substituent variables may be attached to an alkyl linking group when allowed by available valences.

The term "$C_{2-8}$alkenyl" means an alkyl radical or linking group having from 2 up to 8 carbon atoms in a linear or branched arrangement having at least one carbon-carbon double bond. The term "$C_{2-8}$alkenyl" also includes a "$C_{2-4}$alkenyl" radical or linking group having from 2 up to 4 carbon atoms, such as ethenyl (also referred to as vinyl), iso-propenyl, allyl (also referred to as propenyl), propylidene and the like.

The term "$C_{1-8}$alkoxy" means an alkyl radical or linking group having from 1 up to 8 carbon atoms in a linear or branched arrangement, wherein the radical or linking group is attached through an oxygen linking atom, as in the formula: —O—$C_{1-8}$alkyl. The term "$C_{1-8}$alkoxy" also includes a "$C_{1-6}$alkoxy" and "$C_{1-4}$alkoxy" radical or linking group having from 1 up to 6 carbon atoms and from 1 up to 4 carbon atoms respectively, such as methoxy, ethoxy, propoxy, butoxy and the like. An alkoxy radical may be attached to a core molecule and further substituted as a linking group where indicated.

The term "$C_{3-12}$cycloalkyl" means a saturated or partially unsaturated cyclic hydrocarbon ring system radical. The term "$C_{3-12}$cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl or benzofused-$C_{3-12}$cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like.

The term "benzofused-$C_{3-12}$cycloalkyl" means a $C_{3-12}$cycloalkyl ring system radical having a benzene ring fused on the ring system on adjacent carbons. Examples of benzofused-$C_{3-12}$cycloalkyl in compounds representative of the present invention include a benzofused-$C_{5-6}$cycloalkyl ring system radical and the like, such as 1H-indenyl, indanyl and the like.

The term "aryl" means an unsaturated aromatic hydrocarbon ring system radical. Aryl ring systems include phenyl, naphthalenyl, azulenyl, anthracenyl and the like. Examples of aryl in compounds representative of the present invention include phenyl or naphthalenyl.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated "hetero" ring system radical. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepinyl, tetrahydro-furanyl, tetrahydrothienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydrobenzofuranyl, 1,2-dihydro-phthalazinyl and the like.

The term "benzofused-heterocyclyl" means a heterocyclyl ring system radical having a benzene ring fused on the ring system on adjacent carbons. Examples of benzofused-heterocyclyl in compounds representative of the present invention include benzo[1,3]dioxolyl and 2,3-dihydro-indolyl.

The term "heteroaryl" means an unsaturated aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like.

The term "heteroaryl" also includes a benzofused-heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like.

The term "benzofused-heteroaryl" means a heteroaryl ring system radical having a benzene ring fused on the ring system on adjacent carbons. Examples of benzofused-heteroaryl in compounds representative of the present invention include indazolyl, indolyl, benzofuranyl and benzoimidazolyl.

The term "$C_{1-8}$acyl" means a radical of the formula: —C(O)H or —C(O)—$C_{1-8}$alkyl, or a linking group of the formula: —C(O)—$C_{1-8}$alkyl-terminal group.

The term "$C_{1-8}$acyl-amino" means a radical of the formula: —NH—C(O)H or —NH—C(O)—$C_{1-8}$alkyl, or a linking group of the formula: —NH—C(O)—$C_{1-8}$alkyl-terminal group.

The term "$C_{1-8}$alkoxy-$C_{1-8}$alkyl" means a radical of the formula: —$C_{1-8}$alkyl-O—$C_{1-8}$alkyl, or a linking group of the formula: —$C_{1-8}$alkyl-O—$C_{1-8}$alkyl-terminal group.

The term "$C_{1-8}$alkoxy-$C_{1-8}$alkyl-amino-$C_{1-8}$alkyl" means a radical of the formula: —$C_{1-8}$alkyl-NH—$C_{1-8}$alkyl-O—$C_{1-8}$alkyl, —$C_{1-8}$alkyl-N[($C_{1-8}$alkyl)($C_{1-8}$alkyl-O—$C_{1-8}$alkyl)] or —$C_{1-8}$alkyl-N($C_{1-8}$alkyl—O—$C_{1-8}$alkyl)$_2$, or a linking group of the formula: —$C_{1-8}$alkyl-NH—$C_{1-8}$alkyl-O—$C_{1-8}$alkyl-terminal group, —$C_{1-8}$alkyl-N[($C_{1-8}$alkyl)($C_{1-8}$alkyl-O—$C_{1-8}$alkyl-terminal group)], —$C_{1-8}$alkyl-N[($C_{1-8}$alkyl-terminal group)($C_{1-8}$alkyl-O—$C_{1-8}$alkyl)] or —$C_{1-8}$alkyl-N[($C_{1-8}$alkyl)($C_{1-8}$alkyl—O—$C_{1-8}$alkyl-terminal group)].

The term "$C_{1-8}$alkoxycarbonyl" means a radical of the formula: —C(O)—O—$C_{1-8}$alkyl, or a linking group of the formula: —C(O)—O—$C_{1-8}$alkyl-terminal group.

The term "$C_{1-8}$alkoxy-imino-$C_{1-8}$alkyl" means a radical of the formula: —$C_{1-8}$alkyl=N($C_{1-8}$alkoxy).

The term "$C_{1-8}$alkoxy-imino-(aryl)$C_{1-8}$alkyl" means a radical of the formula: —$C_{1-8}$alkyl(aryl)=N($C_{1-8}$alkoxy); wherein the aryl and imino portion is substituted on the same or different $C_{1-8}$alkyl carbon atom.

The term "$C_{1-8}$alkyl-amino" means a radical of the formula: —NH—$C_{1-8}$alkyl or —N($C_{1-8}$alkyl)$_2$.

The term "$C_{1-8}$alkyl-amino-$C_{1-8}$alkyl" means a radical of the formula: —$C_{1-8}$alkyl-NH—$C_{1-8}$alkyl or —$C_{1-8}$alkyl-N($C_{1-8}$alkyl)$_2$, or a linking group of the formula: —$C_{1-8}$alkyl-NH—$C_{1-8}$alkyl-terminal group or —$C_{1-8}$alkyl-N($C_{1-8}$alkyl)-$C_{1-8}$alkyl-terminal group.

The term "$C_{1-8}$alkyl-amino-$C_{1-8}$alkyl-amino-carbonyl" means a radical of the formula: —C(O)—NH—$C_{1-8}$alkyl-NH—$C_{1-8}$alkyl or —C(O)—NH—$C_{1-8}$alkyl-N($C_{1-8}$alkyl)$_2$.

The term "$C_{1-8}$alkyl-sulfonyl-$C_{1-8}$alkyl" means a radical of the formula: —$C_{1-8}$alkyl-SO$_2$—$C_{1-8}$alkyl, or a linking group of the formula: —$C_{1-8}$alkyl-SO$_2$—$C_{1-8}$alkyl-terminal group.

The term "$C_{1-8}$alkyl-sulfonyloxy-$C_{1-8}$alkyl" means a radical of the formula: —$C_{1-8}$alkyl-O—SO$_2$—$C_{1-8}$alkyl, or a linking group of the formula: —$C_{1-8}$alkyl-O—SO$_2$—$C_{1-8}$alkyl-terminal group.

The term "amino" means a radical of the formula: —NH$_2$.

The term "amino-$C_{1-8}$alkyl" means a radical of the formula: —$C_{1-8}$alkyl-NH$_2$, or a linking group of the formula: —$C_{1-8}$alkyl-NH-terminal group or —$C_{1-8}$alkyl-N(terminal group)$_2$.

The term "aryl-amido" means a radical of the formula: —NHC(O)-aryl.

The term "aryl-amino" means a radical of the formula: —NH-aryl.

The term "aryl-$C_{1-8}$alkyl" means a radical of the formula: —$C_{1-8}$alkyl-aryl.

The term "aryl-carbonyl-$C_{1-8}$alkyl" means a radical of the formula: —$C_{1-8}$alkyl-C(O)-aryl.

The term "aryl-$C_{1-8}$alkoxy" means a radical of the formula: —O—$C_{1-8}$alkyl-aryl.

The term "aryloxy" means a radical of the formula: —O-aryl.

The term "aryloxy-$C_{1-8}$alkyl" means a radical of the formula: —$C_{1-8}$alkyl-O-aryl.

The term "carboxy" means a radical of the formula: —C(O)OH.

The term "cyano-$C_{1-8}$alkyl" means a radical of the formula: —$C_{1-8}$alkyl-C≡N.

The term "halogen" or "halo" means the group chloro, bromo, fluoro or iodo.

The term "halo-$C_{1-8}$alkoxy" means a radical of the formula: —$C_{1-8}$alkoxy(halo)$_{1-17}$, wherein one or more halogen atoms may be substituted on $C_{1-8}$alkoxy when allowed by available valences and includes monofluoromethoxy, difluoromethoxy, trifluoromethoxy, trifluoroethoxy and the like.

The term "halo-$C_{1-6}$alkoxy" means a radical of the formula: —$C_{1-6}$alkoxy(halo)$_{1-13}$, wherein one or more halogen atoms may be substituted on $C_{1-6}$alkoxy when allowed by available valences.

The term "halo-$C_{1-8}$alkyl" means a radical of the formula: —$C_{1-8}$alkyl(halo)$_{1-17}$, wherein one or more halogen atoms may be substituted on $C_{1-8}$alkyl when allowed by available valences and includes monofluoromethyl, difluoromethyl, trifluoromethyl, trifluoroethyl and the like.

The term "halo-$C_{1-6}$alkyl" means a radical of the formula: —$C_{1-6}$alkyl(halo)$_{1-13}$, wherein one or more halogen atoms may be substituted on $C_{1-6}$alkyl when allowed by available valences.

The term "heterocyclyl-$C_{1-8}$alkyl" means a radical of the formula: —$C_{1-8}$alkyl-heterocyclyl.

The term "heterocyclyl-carbonyl-$C_{1-8}$alkyl" means a radical of the formula: —$C_{1-8}$alkyl-C(O)-heterocyclyl.

The term "heteroaryl-$C_{1-8}$alkoxy" means a radical of the formula: —O—$C_{1-8}$alkyl-heteroaryl.

The term "heteroaryl-$C_{1-8}$alkyl" means a radical of the formula: —$C_{1-8}$alkyl-heteroaryl.

The term "heteroaryl-amino-sulfonyl" means a radical of the formula: —SO$_2$—NH-heteroaryl.

The term "heteroaryloxy" means a radical of the formula: —O-heteroaryl.

The term "hydroxy-$C_{1-8}$alkoxy" means a radical wherein $C_{1-8}$alkoxy is substituted on an available carbon chain atom with one or more hydroxy radicals.

The term "hydroxy-$C_{1-8}$alkyl" means a radical wherein $C_{1-8}$alkyl is substituted on an available carbon chain atom with one or more hydroxy radicals.

The term "thio-$C_{1-8}$alkyl" means a radical of the formula: —S—$C_{1-8}$alkyl.

The term "substituted" means the independent replacement of one or more hydrogen atoms within a radical with that amount of substituents allowed by available valences.

In general, IUPAC nomenclature rules are used herein.

Compound Forms

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "aqueous solvent" means water used as a solvent or water substantially in a mixture with one or more other solvents.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-nitrogen double bond. In the "Z" configuration, the substituents are oriented on the same side in relationship to the carbon-nitrogen double bond.

As illustrated by:

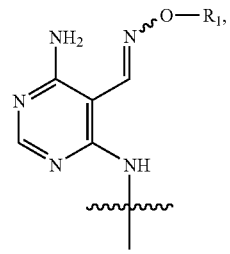

the wave line between the double bond nitrogen atom and the O—R$_1$ substituent for certain compounds of the present invention is intended to represent that the orientation of the O—R$_1$ substituent atoms in relationship to the carbon-carbon double bond are not designated either E or Z. Accordingly, the illustrated bond lines and orientation implies that the substituent atoms may be in either the E or Z configuration. All such configurations are intended to be included within the scope of the present invention.

The isomeric descriptors ("R," "S," "E," and "Z") indicate atom configurations and are intended to be used as defined in the literature.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

SYNTHETIC EXAMPLES

General Synthetic Methods

Representative compounds of the present invention can be synthesized in accordance as illustrated in the specific synthetic examples that follow. The specific examples are offered by way of illustration; the invention should not be construed as being limited by the chemical reactions and conditions expressed. The methods for preparing the various starting materials used in the examples are well within the skill of persons versed in the art. No attempt has been made to optimize the yields obtained in any of the example reactions. One skilled in the art would know how to increase such yields through routine variations in reaction times, temperatures, solvents and/or reagents. Furthermore, reaction time is that length of time one skilled in the art would typically allow a reaction to run until HPLC analysis shows the reaction is complete.

The terms used in describing the invention are commonly used and known to those skilled in the art. When used herein, the following abbreviations have the indicated meanings:

| Abbreviation | Meaning |
| --- | --- |
| ACN | acetonitrile |
| cat. | catalytic |
| Cpd | compound |
| DMF | N,N-dimethylformamide |
| Eq, Eq. or Equiv. | equivalent, equivalents or equivalence |
| EtOH | ethanol |
| h/hr(s)/min(s) | hour(s)/min(s) |
| HPLC | High Pressure Liquid Chromatography |
| iPA or IPA | isopropanol |
| mp | melting point |
| MeOH | methanol |
| 2-Me-THF | 2-methyl-tetrahydrofuran |
| nm | nanometer |
| nd | not detected |
| nPA | 1-propanol |
| NMP | N-methyl-pyrrolidinone |
| 2-OMe-EtOH | 2-methoxy-ethanol |
| RT/rt/r.t. | room temperature |
| TEA | triethylamine |
| THF | tetrahydrofuran |
| v/v | volume/volume |

Example 1

(5E)-4-amino-6-(4-benzyloxy-3-chloro-phenylamino)-pyrimidine-5-carbaldehyde O-(2-morpholin-4-yl-ethyl)-oxime mono-hydrochloride salt (Cpd 78*)

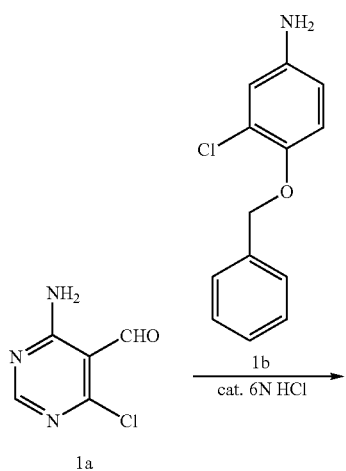

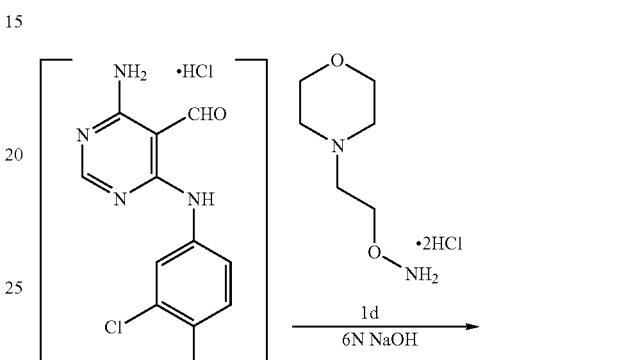

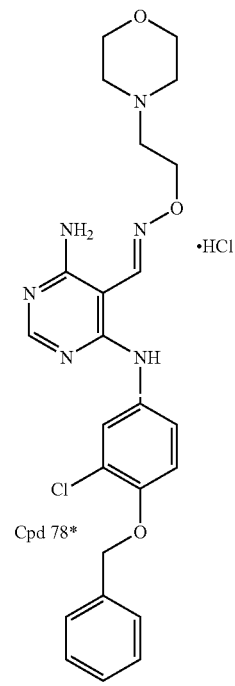

20 minutes at about 37-43° C. and then heated to about 62-70° C. During this period, the mixture became very thick but remained stirrable. After aging, the mixture became thinner as the reaction reached about 85% conversion in about 30 minutes at about 65° C. The reaction included the formation of compounds (5) —N-(4-benzyloxy-3-chloro-phenyl)-5-[(4-benzyloxy-3-chloro-phenylimino)-methyl]-pyrimidine-4,6-diamine Compound AA3 and (5)-5-[(4-benzyloxy-3-chloro-phenylimino)-methyl]-6-chloro-pyrimidin-4-ylamine Compound AA4. As the mixture was aged, the starting materials converted to the title Compound 1c used in the next step as an unisolated intermediate.

Step 1. 4-amino-6-(4-benzyloxy-3-chloro-phenylamino)-pyrimidine-5-carbaldehyde Cpd 1c To a 500 ml 3-neck flask equipped with thermo-couple, water condenser with nitrogen adaptor and overhead stirrer was added 4-benzyloxy-3-chloro-phenylamine Compound 1b (5.00 g, 21.4 mmol), 4-amino-6-chloro-pyrimidine-5-carbaldehyde Compound 1a (19.39 g, 114.5 mmol), 2-methoxyethanol (225 ml) and deionized water (25 ml). The resulting very thin slurry was stirred and 6N HCl (1.78 ml, 10.7 mmol) was added. As a yellow precipitate was formed, the reaction mixture was heated to about 37-43° C. and stirred for about 15 to 20 minutes. A second addition of Compound 1b (10.00 g, 42.8 mmol) was made and the reaction mixture was stirred for about 15 to 20 minutes at about 37-43° C. After about 5 minutes, the suspended solids dissolved and within a few additional minutes, precipitation produced a thick suspension. A third addition of Compound 1b (10.00 g, 42.8 mmol) was made and the reaction mixture was stirred for about 15 to Step 2. (5E)-4-amino-6-(4-benzyloxy-3-chloro-phenylamino)-pyrimidine-5-carbaldehyde O-(2-morpholin-4-yl-ethyl)-oxime Compound 78* mono-hydrochloride salt The reaction mixture containing Compound 1c was cooled to about 20-25° C., then O-(2-morpholin-4-yl-ethyl)-hydroxylamine dihydrochloride Compound 1d (30.39 g, 112.3 mmol) and a 6.0N NaOH solution (39.2 ml, 235.4 mmol) was added. The resulting slurry was heated to about 100-115° C. and a distillate (between about 125-166 ml at 1 atmosphere) was collected. The slurry became very thick at a temperature of about 65-85° C., and was much thinner at greater than 85° C. At 100-105° C. the slurry became a clear light brown to dark orange solution. The reaction mixture was stirred for about 5 hours at about 100-115° C., until the ratio of the E/Z isomers was >45:1 by HPLC at 248 nm.

The mixture was cooled to about 20-25° C. and 2-methoxy-ethanol (62 ml) and deionized water (62 ml) were added. The resulting suspension was stirred for about 30 minutes. 2-methoxyethanol/water was added to the suspension to dissolve NaCl that was formed in the reaction, thus thinning the slurry for filtration. The thinned slurry was filtered using a Buchner funnel. The reactor was rinsed with 2-methoxy-ethanol:water mixture (1:1, 50 ml). The filter cake was then washed once with the reactor rinse, two times with a fresh 2-methoxy-ethanol:water mixture (1:1, 50 ml) and two times with a 1-propanol:water:mixture (1:1, 50 ml). The wet cake was dried thoroughly on the filter, transferred to a crystallizing dish and dried under vacuum at about 55-65° C. until the product weight was constant to provide the title Compound 78* mono-hydrochloride salt (45.21 g) as a light yellow crystalline powder.

Step 3. Recrystallization

To a 3 L, four-necked round bottom flask equipped with an overhead stirrer, condenser with nitrogen inlet, and a thermocouple was added Compound 78* (200.0 g, 0.385 mol), 1-propanol (1000 ml) and deionized water (1000 ml). The resulting suspension was heated at about 70° C. until a clear solution was achieved (at about 40° C., the solution becomes turbid). The warm solution was filtered using a medium-glass sintered funnel with filter paper. The solution can be held for 60-90 minutes at 60-65° C. without precipitation. The slurry can be redissolved at about 70° C. if the solid prematurely precipitates.

The solution was cooled to about 10° C. over a period of about 3.5 hours and then held at about 10° C. for about one hour. The suspension was filtered again using a coarse-sintered glass funnel with filter paper. The reactor was rinsed with a 1-propanol:water wash (1:1, 400 ml). The filter cake was washed once with the rinse and again with a fresh 1-propanol:water wash (400 ml). The filter cake was air-dried for at least 30 minutes, then dried under vacuum at about 55-60° C. until the product weight was constant to provide the title Compound 78* mono-hydrochloride salt (169.5 g) as a light yellow crystalline solid.

$^1$H NMR (300 MHz, DMSO-d6): 10.92 (bs, 1H), 9.51 (s, 1H), 8.78 (s, 1H), 8.05 (s, 1H), 7.83 (bs, 1H), 7.48-7.34 (m, 6H), 7.18 (d, J=6 Hz, 1H), 5.20 (s, 2H), 4.59 (bt, 2H), 3.94-3.17 (series of m, 12H).

Example 2

4-amino-6-(4-benzyloxy-3-chloro-phenylamino)-pyrimidine-5-carbaldehyde mono-hydrochloride salt (Cpd 1c)

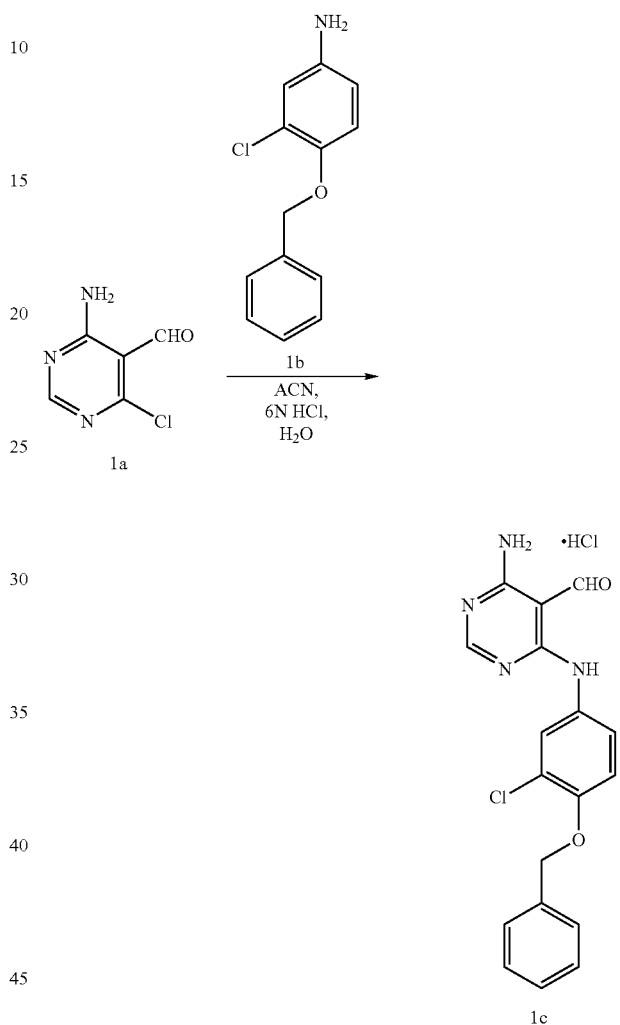

To a 10 ml 1N flask equipped with nitrogen inlet and thermocouple was added Cpd 1a (1 mmol), Cpd 1b (1 mmol) and acetonitrile (1.4 ml). The mixture was stirred, then 6N HCl (15 μl) and H$_2$O (0.1 ml) were added. The mixture was stirred at a temperature of about 70-75° C. for 4 h and cooled naturally to ambient temperature. The precipitated product was filtered via filter paper using a sintered funnel and the reaction flask was rinsed ×2 with acetonitrile (0.5 ml). The rinse was used to wash the filter cake. The solids were washed with fresh acetonitrile (0.5 ml) then dried in a vacuum oven until a constant weight was obtained to provide the title Cpd 1c as a mono-HCl acid salt (91% yield).

$^1$H NMR (300 MHz, DMSO-d6): 11.28 (s, 1H), 10.23 (s, 1H), 8.33 (s, 1H), 7.45 (d, J=8.4 Hz, 2H), 7.75 (d, J=2.5 Hz, 1H), 7.49-7.25 (m, 8H), 5.23 (s, 2H), 4.5 (b, 2H). MS (ES+): mass calc'd. for $C_{18}H_{16}Cl_2N_4O_2$, 391.25; m/z found 390.3 [M−H].

Using the procedure of Example 2 and the appropriate reagents, starting materials and reaction conditions known to those skilled in the art, other intermediates representative of the scope of the present invention were prepared:

| Cpd | Name |
|---|---|
| 1c-1 | 4-amino-6-(3-chloro-4-fluoro-phenylamino)-pyrimidine-5-carbaldehyde (87% yield); $^1$H NMR (300 MHz, DMSO-d6): 11.09 (s, 1H), 10.20 (s, 1H), 8.29 (s, 1H), 7.95 (dd, J = 6.8 & 3 Hz, 1H), 7.56-7.41 (m, 3H), 6.00 (bs, 2H). MS (ES+): mass calc'd. for $C_{11}H_9Cl_2FN_4O$, 303.14; m/z found 302.1 [M − H]. |
| 1c-2 | 4-amino-6-(4-bromo-3-fluoro-phenylamino)-pyrimidine-5-carbaldehyde (85% yield); $^1$H NMR (300 MHz, DMSO-d6): 11.43 (s, 1H), 10.28 (s, 1H), 9.00-8.5 (bs, 2H), 8.32 (s, 1H), 7.95 (t, J = 8.6 Hz, 1H), 7.7 (dd, J = 10.3 & 2.2 Hz, 1H), 7.48 (d, J = 9.8 Hz, 1H). MS (ES+): mass calc'd. for $C_{11}H_9BrClFN_4O$, 347.57; m/z found 348.6 [M + H+]. |
| 1c-3 | 4-amino-6-(4-ethyl-phenylamino)-pyrimidine-5-carbaldehyde (74% yield); $^1$H NMR (300 MHz, DMSO-d6): 11.32 (s, 1H), 10.21 (s, 1H), 8.7 (broad peak, 3H), 8.30 (s, 1H), 7.45 (d, J = 8.4 Hz, 2H), 7.25 (d, J = 8.4 Hz, 2H), 2.50 (q, J = 3.5 & 1.8 Hz, 2H), 1.2 (t, J = 7.6 Hz, 3H). MS (ES+): mass calc'd. for $C_{13}H_{15}ClN_4O$, 278.74; m/z 277.7 [M − H]. |
| 1c-4 | 4-amino-6-(4-phenoxy-phenylamino)-pyrimidine-5-carbaldehyde (85% yield); $^1$H NMR (300 MHz, DMSO-d6): 11.30 (s, 1H), 10.23 (s, 1H), 8.31 (s, 1H), 7.58-7.02 (series of m, 10H), 9.10 (b, 2H). MS (ES+): mass calc'd. for $C_{17}H_{15}ClN_4O_2$, 342.78; m/z found 341.1 [M − H]. |
| 1c-5 | 4-amino-6-phenylamino-pyrimidine-5-carbaldehyde $^1$H NMR (300 MHz, DMSO-d6): 11.32 (s, 1H), 10.24 (s, 1H), 8.31 (s, 1H), 7.59-7.30 (series of m, 5H), 3.7 (b, 3H). MS (ES+): mass calc'd. for $C_{11}H_{11}ClN_4O$, 250.68; m/z found 228.1 [M − HCl − H]. |
| 1c-6 | 4-amino-6-(2-amino-phenylamino)-pyrimidine-5-carbaldehyde (52% yield); $^1$H NMR (300 MHz, DMSO-d6): 13.19 (s, 1H), 9.14 (s, 1H), 8.40 (s, 1H), 8.38 (s, 1H), 8.34 (s, 1H), 8.29 (bs, 1H), 7.55 (d, J = 7.6 Hz, 1H), 7.43-7.16 (2m, 2H), 3.8 (b, 3H). MS (ES+): mass calc'd. for $C_{11}H_{11}ClN_3O$, 265.7; m/z found 228.2 [M − HCl − H]. |
| 1c-7 | 4-amino-6-(3-fluoro-phenylamino)-pyrimidine-5-carbaldehyde (89% yield); $^1$H NMR (300 MHz, DMSO-d6): 11.37 (s, 1H), 10.24(s, 1H), 8.36 (s, 1H), 7.66-7.01 (series of multiplet, 4H). 6.00 (bs, 3H). MS (ES+): mass calc'd. for $C_{11}H_{10}ClN_4O$, 268.67; m/z 233.2. found [M − HCl + H]. |
| 1c-8 | 4-amino-6-(3,5-dimethoxy-phenylamino)-pyrimidine-5-carbaldehyde (87% yield); $^1$H NMR (300 MHz, DMSO-d6): 10.45 (s, 1H), 10.15 (s, 1H), 9.72 (s, 1H), 8.82 (s, 1H), 6.97 (bs, 1H), 6.79 (bs, 1H), 4.07 (s, 3H), 4.02 (s, 3H), 3.60 (bs, 3H). MS (ES+): mass calc'd. for $C_{13}H_{15}ClN_4O_3$, 310.74; m/z 297.3 found 297.3 [M − HCl + Na]. |
| 1c-9 | 4-amino-6-(4-nitro-phenylamino)-pyrimidine-5-carbaldehyde (88% yield); $^1$H NMR (300 MHz, DMSO-d6): 11.53 (s, 1H), 10.28 (s, 1H), 9.00 (bs, 3H), 8.42 (s, 1H), 8.26 (d, J = 9.2 Hz, 2H) 7.85 (d, J = 9.2, 2H) (ES+): mass calc'd. for $C_{11}H_{10}ClN_5O_3$, 295.68; m/z found 296.7 [M + H]. |

Example 3

(5E)-4-amino-6-(4-benzyloxy-3-chloro-phenylamino)-pyrimidine-5-carbaldehyde O-(2-morpholin-4-yl-ethyl)-oxime (Cpd 78) (free base)

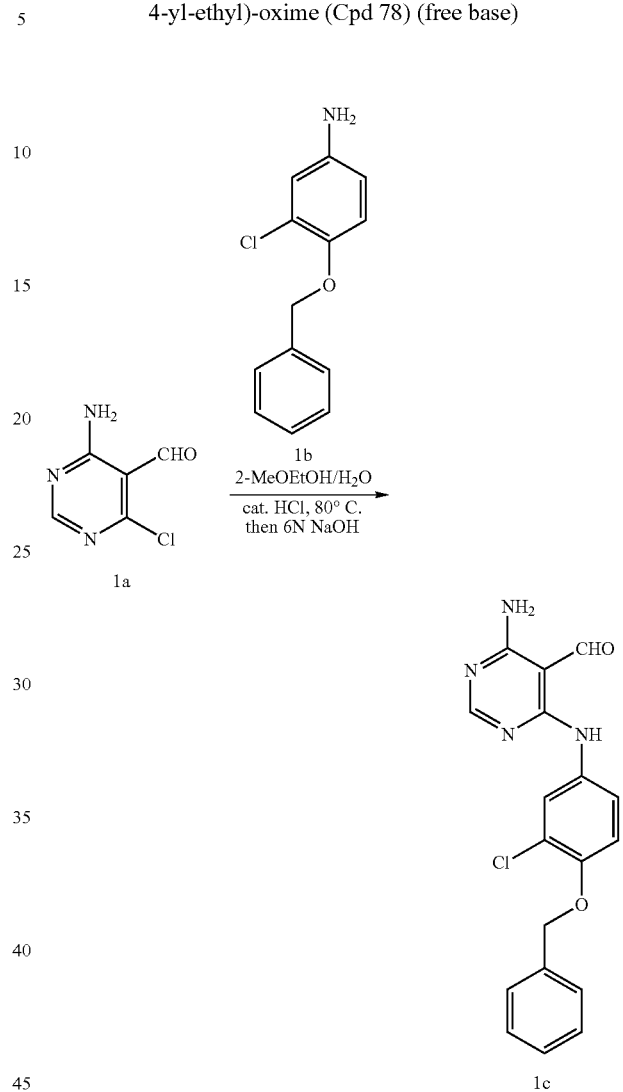

Step 1. 4-amino-6-(4-benzyloxy-3-chloro-phenylamino)-pyrimidine-5-carbaldehyde Cpd 1c (isolated free base)

In a 3-necked round bottom flask equipped with a thermal couple, an overhead stirrer and a condenser was added 4-amino-6-chloro-pyrimidine-5-carbaldehyde Cpd 1a (3.23 g, 19.0 mmol), 4-benzyloxy-3-chloro-phenylamine Cpd 1b (4.24 g, 18.1 mmol), 2-methoxyethanol (27 ml) and water (3 ml). The mixture was stirred at room temperature and a 6N HCl solution (0.30 ml, 0.10 eq.) was added. The mixture was heated to 80° C. for 1-2 hours until the starting materials were consumed. The mixture was cooled to room temperature and 6 N NaOH solution (3.3 ml) and water (8 ml) were added. The mixture was cooled to room temperature again and the solid was collected by vacuum filtration. The reaction flask was rinsed by 1:1 EtOH:water (2×10 ml) and the rinses were used to wash the filter cake. The filter cake was further washed by 1:1 EtOH:water (2×10 ml), suction dried, dried in an vacuum oven at 60° C. under house vacuum to afford the title Compound 1c free base as a light yellow solid (6.06 g). $^1$H NMR (400 MHz, DMSO-d6) δ 10.66 (s, 1H), 10.14 (s, 1H), 8.11 (s, 1H), 7.90 (bs, 1H), 7.88 (d, J=2.0 Hz, 1H), 7.48-7.32 (m, 5H), 7.21 (d, J=8.0 Hz, 1H), 5.20 (s, 2H), 3.24 (bs, 2H); mp 206° C. (by DSC).

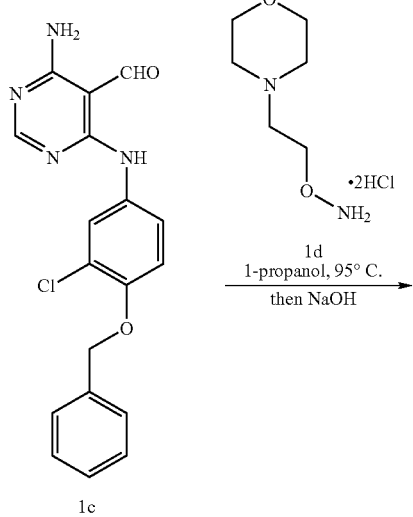

J=5.6 Hz, 2H), 3.58 (m, 4H), 2.66 (t, J=5.6 Hz, 2H), 2.47 (m, 4H); MS (ESI) m/z 383 (MH+); mp 176° C. (by DSC).

Example 4

(5E)-4-amino-6-(4-benzyloxy-3-chloro-phenylamino)-pyrimidine-5-carbaldehyde O-(2-morpholin-4-yl-ethyl)-oxime (Cpd 78**) (bis-hydrochloride salt)

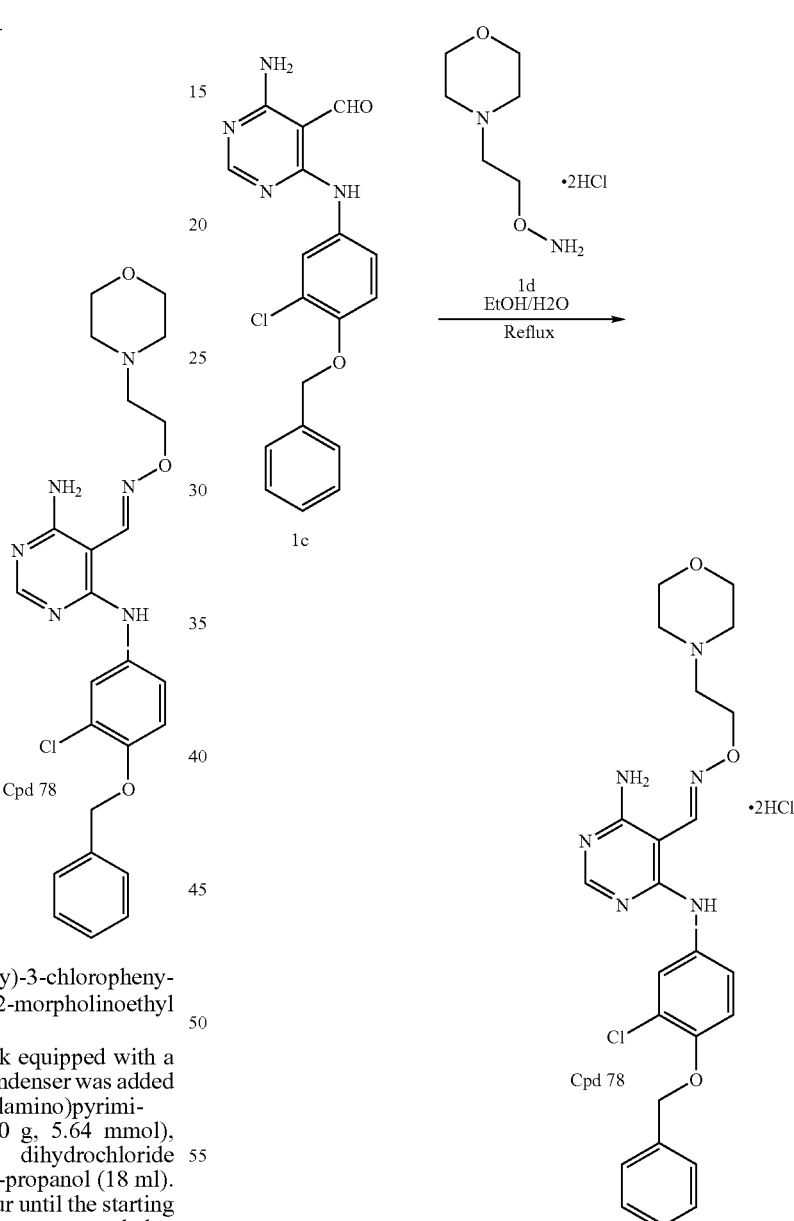

Step 2. (5E)-4-amino-6-(4-(benzyloxy)-3-chlorophenylamino)pyrimidine-5-carbaldehyde O-2-morpholinoethyl oxime Cpd 78 (free base)

In a 50 ml 3-necked round bottom flask equipped with a magnetic stirrer, a thermal couple and a condenser was added 4-amino-6-(4-(benzyloxy)-3-chlorophenylamino)pyrimidine-5-carbaldehyde Compound 1c (2.00 g, 5.64 mmol), O-(2-morpholinoethyl)hydroxylamine dihydrochloride Compound 1d (1.36 g, 6.20 mmol), and 1-propanol (18 ml). The mixture was heated at 95° C. for 1 hour until the starting material aldehyde was consumed. The mixture was cooled to room temperature and 6 N NaOH solution (2.07 ml, 12.4 mmol) and water (17.5 ml) were added with stirring. The resulted slurry was stirred and cooled to room temperature and the solid was collected by vacuum filtration. The filter cake was washed with water (2×10 ml), suction dried and dried in a vacuum oven at 60° C. under house vacuum to afford the title Compound 78 free base as a light yellow solid (2.49 g). $^1$H NMR (300 MHz, DMSO-d6) δ 9.60 (s, 1H), 8.72 (s, 1H), 8.03 (s, 1H), 7.83 (d, J=2.7 Hz, 1H), 7.49-7.39 (m, 6H), 7.28 (s, 2H), 7.18 (d, J=9.0 Hz, 1H), 5.20 (s, 2H), 4.30 (t, In a 100 ml, 3 N round bottom flask equipped with magnetic stirring bar, thermocouple, water condenser with nitrogen inlet was added Compound 1c (1 g, 2.81 mmol), Compound 1d (0.63 g, 3 mmol, 1.1 equiv), 11 ml of EtOH and 0.58 ml of H$_2$O and the mixture was stirred. The resulting suspension was heated to 80° C. and went into solution. The mixture was held at 80° C. for 2.5 h and 1.5 ml of solvent was distilled off. The mixture was allowed to cool to ambient temperature overnight. The solids were filtered off via a glass-sintered funnel having a filter paper on top. The reaction flask was rinsed with 3.5 ml of EtOH and the rinse was used to wash the filter cake. The solids were dried in a laboratory vacuum oven at 55° C. until a constant weight was obtained, to provide the title Compound 78** bis-hydrochloride salt as an off white solid (1.34 g). DSC peak 227.3° C. Anal. calc'd for $C_{24}H_{29}Cl_3N_6O_3$:C, 51.86; H, 5.26; N, 15.12, Cl, 19.13. Found: C, 51.34; H, 5.18; N, 15.12; Cl, 21.12. $^1$H NMR (300 MHz, DMSO-d6): 10.92 (bs, 1H), 9.51 (s, 1H), 8.78 (s, 1H), 8.05 (s, 1H), 7.83 (bs, 1H), 7.48-7.34 (m, 6H), 7.18 (d, J=6 Hz, 1H), 5.20 (s, 2H), 4.59 (bt, 2H), 3.94-3.17 (series of m, 12H).

Example 5

(5E)-4-amino-6-(4-benzyloxy-3-chloro-phenylamino)-pyrimidine-5-carbaldehyde O-(2-morpholin-4-yl-ethyl)-oxime mono-hydrochloride salt (Cpd 78*)

kg), 4-amino-6-chloro-pyrimidine-5-carbaldehyde Compound 1a (5.98 kg), 4-benzyloxy-3-chloro-phenylamine Compound 1b (5.98 kg), 6N HCl (1.54 kg) and purified water (0.55 kg). The reactor wall was rinsed with 2-methoxy-ethanol (0.5 kg). The slurry was heated to about 40° C. and aged for 15 minutes. A second addition of Compound 1b (3.09 kg) was made and the reaction mixture was aged for an additional 15 minutes. The slurry solution then crystallized. A third addition of Compound 1b (3.08 kg) was made and the reaction mixture was aged for 15 minutes. The slurry was heated to about 65° C. until HPLC analysis showed the reaction was complete, thus providing 4-amino-6-(4-benzyloxy-3-chloro-phenylamino)-pyrimidine-5-carbaldehyde Compound 1c which was used in the next step as an unisolated intermediate.

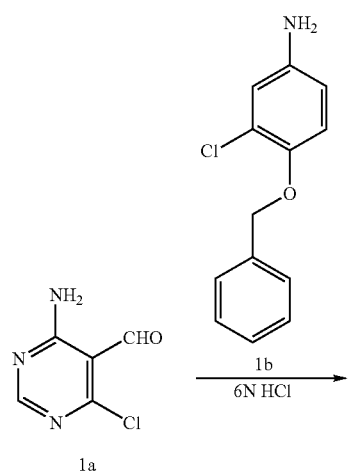

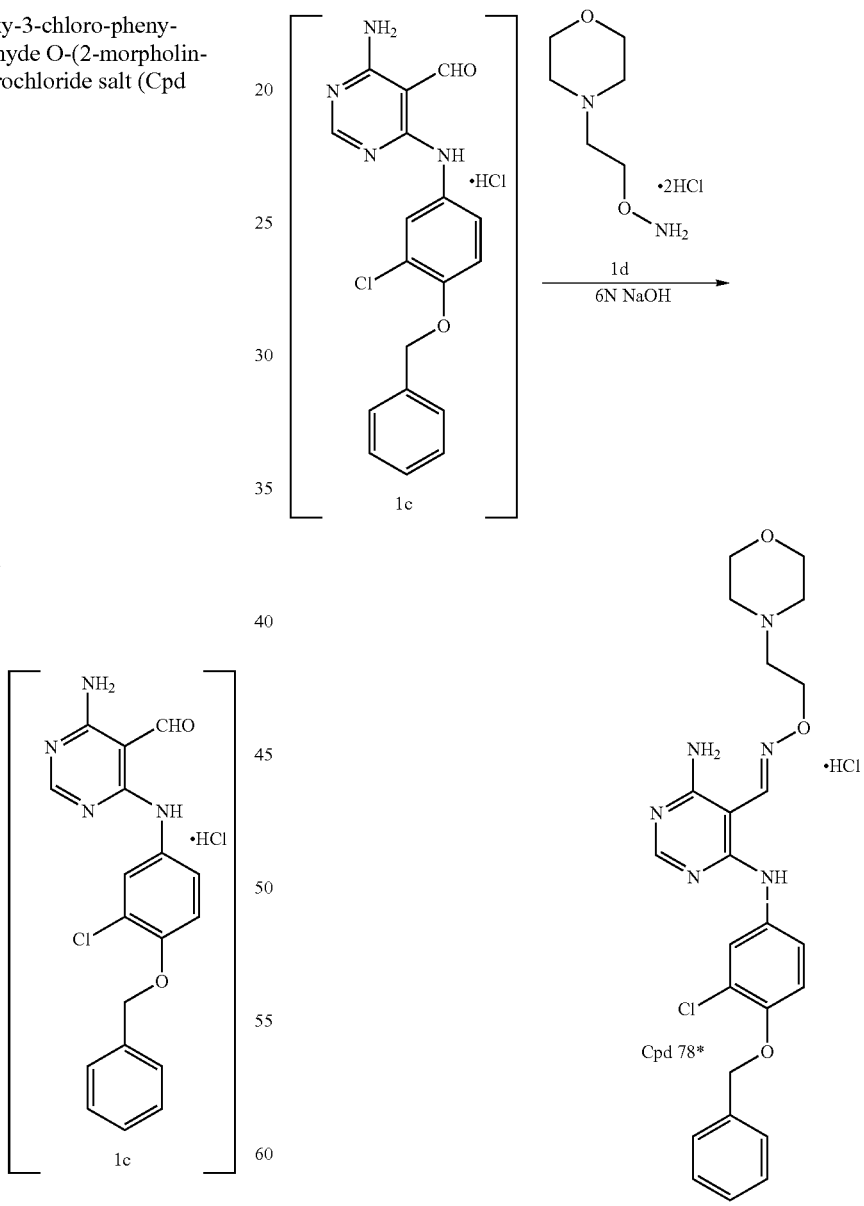

The following example was disclosed as Example 4 in the commonly assigned U.S. patent application Ser. No. 11/609,450, filed Dec. 12, 2006.

To a 100 L reactor equipped with nitrogen sweep, thermocouple and condensers was added 2-methoxy-ethanol (66.5

The slurry containing Compound 1c was cooled to between about 20-25° C., then O-(2-morpholin-4-yl-ethyl)-hydroxylamine dihydrochloride Compound 1d (9.37 kg) and 6.0N NaOH solution (12.1 L) was added. The suspension was heated to reflux between about 105° C. to about 115° C. and the distillate (between about 38.5 to about 43.5 kg) was collected. The slurry was cooled to between about 20° C. to about 25° C., then 2-methoxy-ethanol (18.5 kg) and purified water (19.1 kg) was added. The resulting slurry was stirred for 0.5 h, then filtered on an 18" polypropylene filter lined with polypropylene cloth. The filter cake was washed thrice with a mixture (1:1 v/v) of 2-methoxy-ethanol (15.1 kg) and water (13.9 kg). The wet cake was dried on the filter for at least 30 minutes then transferred to polypropylene drying trays, weighed and covered with polypropylene tray covers. The product was dried to a constant weight at between about 55° C. to about 60° C. under vacuum with a nitrogen bleed to provide Compound 78* (13.79 kg, 81% yield) as a yellow powder. 98.9 HPLC Area %, 99.6 HPLC wt. % vs. standard.

Compound 78* (11.00 kg), 1-propanol (44.2 kg) and water (55.0 kg) was added to a 100 L reactor equipped with nitrogen sweep, thermocouple, and condensers. The resulting suspension was heated until a solution was achieved (at about 70° C.). The solution was cooled to between about 60° C. to about 65° C. and the contents were filtered to another 100 L reactor using a 145-175 micron filter. The solution was cooled to about 10° C. over a period of about 3.5 hours and then aged for about one hour. The suspension was filtered on an 18" polypropylene filter lined with polypropylene cloth and the resulting cake was washed twice each with a 1:1 (v/v) mixture of 1-propanol/water (19.8 kg). The filter cake was dried with nitrogen for at least 30 minutes on the filter and then transferred to polypropylene drying trays, weighed and covered with polypropylene tray covers. The product was dried to a constant weight at between about 55° C. to about 60° C. under vacuum with a nitrogen bleed to provide the title Compound 78* (9.60 kg, 87% yield) mono-hydrochloric acid salt as a light yellow powder. 99.0 HPLC Area %, 99.8 HPLC wt. % vs. standard.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. These publications are hereby incorporated by reference in their entirety into this application to describe more fully the state of the art to which this invention pertains.

What is claimed is:

1. A process for preparing a compound of Formula (I) and an acid salt thereof:

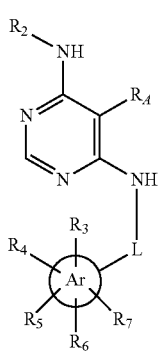

I wherein

L is selected from a bond, $C_{1-6}$alkyl or F—$C_{1-6}$alkyl;

Ar is selected from aryl, heteroaryl, benzofused-heterocyclyl or benzofused-$C_{3-12}$cycloalkyl;

$R_A$ is selected from C=N—O—$R_1$;

$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, F—$C_{1-8}$alkyl, F—$C_{1-8}$alkoxy, cyano-$C_{1-8}$alkyl, $C_{3-12}$cycloalkyl, aryl, aryloxy, aryl-$C_{1-8}$alkyl, aryl-$C_{1-8}$alkoxy, heteroaryl, heteroaryloxy, heteroaryl-$C_{1-8}$alkoxy, benzofused-heterocyclyl or heterocyclyl, wherein aryl, aryloxy, aryl-$C_{1-8}$alkyl and aryl-$C_{1-8}$alkoxy is each optionally substituted on aryl with one, two, three, four or five substituents each selected from cyano, halogen, $C_{1-8}$alkyl, $C_{1-8}$alkoxy, or $C_{1-8}$alkoxycarbonyl, wherein benzofused-heterocyclyl is optionally substituted on the heterocyclyl portion with one or two oxo substituents, and wherein heteroaryl, and heteroaryloxy is each optionally substituted on heteroaryl with one, two, three, four or five substituents each selected from $C_{1-8}$alkyl or $C_{1-8}$acyl;

comprising the steps of:

Step 1. reacting a Compound 1a** (wherein Ra represents a halogen leaving group), a Compound A1 in an aqueous solvent and a catalytic amount of acid to provide a Compound A2 acid salt:

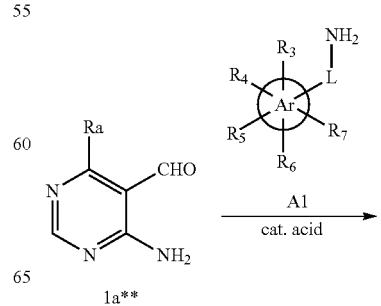

1a**

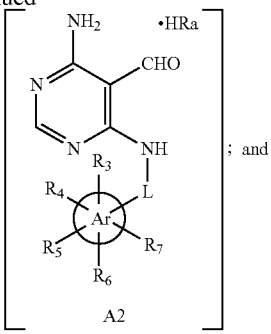

Step 2. reacting the Compound A2 acid salt with a Compound A3 bis-acid salt (wherein the acid of the bis-acid salt is HRa) and a base to provide a Compound A4 acid salt, representative of a compound of Formula (I):

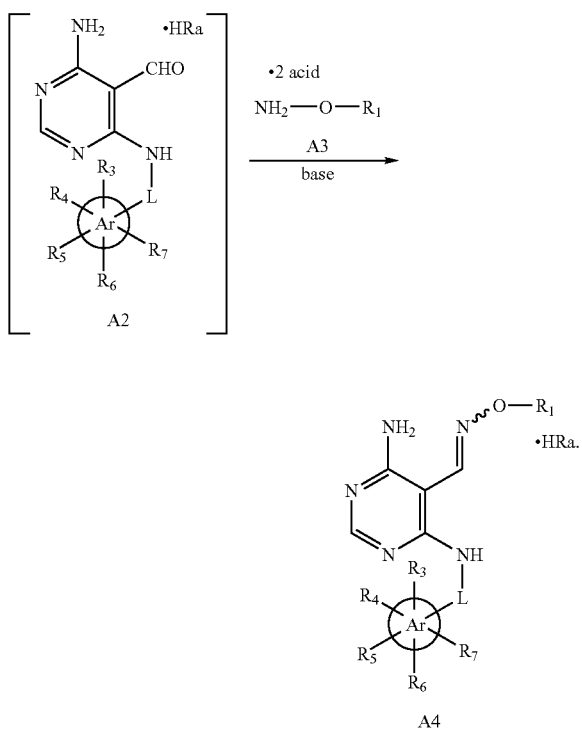

2. The process of claim 1, wherein a mixture of geometric isomers of the Compound A4 is formed.

3. The process of claim 2, wherein the Compound A4 E-isomer is obtained.

4. The process of claim 1, wherein one of the solvents used in Step 1 of the reaction is water and the other is optionally selected from isopropanol, 2-methoxy-ethanol, 1-propanol, methanol, ethanol, 1-butanol, THF, 2-Me-THF, toluene or acetonitrile.

5. The process of claim 4, wherein one of the solvents used in Step 1 is water and the other is optionally selected from isopropanol, 2-methoxy-ethanol, 1-propanol or acetonitrile.

6. The process of claim 5, wherein the solvent used in Step 1 is water.

7. The process of claim 5, wherein the solvent used in Step 1 is water and the other is 2-methoxy-ethanol.

8. The process of claim 1, wherein the amount of water is at least 0.005 molar equivalents (wherein the molar equivalence is based on Compound A1).

9. The process of claim 8, wherein the amount of water is in a range of from about 1 molar equivalent to about 99 molar equivalents (wherein the molar equivalence is based on Compound A1).

10. The process of claim 9, wherein the amount of water is in a range of from about 1 molar equivalent to about 26 molar equivalents (wherein the molar equivalence is based on Compound A1).

11. The process of claim 10, wherein the amount of water is in a range of from about 1 molar equivalent to about 13 molar equivalents (wherein the molar equivalence is based on Compound A1).

12. The process of claim 1, wherein the amount of solvent and the amount of water used in Step 1 are in a ratio, wherein the ratio is in a range of from 6:5 (v/v) to about 11:1 (v/v) solvent:water.

13. The process of claim 12, wherein the solvent to water ratio used in Step 1 is a ratio of about 11:1 (v/v) solvent:water, or is a ratio of about 9:1 (v/v) solvent:water, or is a ratio of about 9:2 (v/v) solvent:water, or is a ratio of about 8:3 (v/v) solvent:water, is a ratio of about 8:2 (v/v) solvent:water, or is a ratio of about 7:4 (v/v) solvent:water, or is a ratio of about 6:5 (v/v) solvent:water.

14. The process of claim 13, wherein the solvent to water ratio used in Step 1 is a ratio of about 9:1 (v/v) solvent:water.

15. The process of claim 1, wherein the amount of aqueous solvent is in a range of from about 6 ml to about 76 ml per 1 g of Compound A1.

16. The process of claim 15, wherein the amount of aqueous solvent is in a range of from about 9 ml to about 11 ml per 1 g of Compound A1.

17. The process of claim 16, wherein the amount of aqueous solvent is about 10 ml per 1 g of Compound A1.

18. The process of claim 1, wherein the catalytic amount of acid used is in a range of from about 0.01 molar equivalents to about 2 molar equivalents, wherein the molar equivalence is based on Compound A1.

19. The process of claim 18, wherein the catalytic amount of acid is in a range of from about 0.01 molar equivalents to about 0.15 molar equivalents, wherein the molar equivalence is based on Compound A1.

20. The process of claim 19, wherein the catalytic amount of acid is in a range of from about 0.1 molar equivalents to about 0.15 molar equivalents, wherein the molar equivalence is based on Compound A1.

21. The process of claim 1, wherein the acid used is HCl, wherein Ra in Compound 1a is chloro or, alternatively, HBr, wherein Ra in Compound 1a is bromo.

22. The process of claim 1, wherein the water and the solvent used in Step 1 are mixed prior to the addition of other reactants, thus forming an aqueous solvent.

23. The process of claim 1, wherein the water and the catalytic amount of acid used in Step 1 are mixed prior to the addition of other reactants, thus forming an aqueous acid.

24. The process of claim 1, wherein the Compound 1a** and the aqueous solvent are mixed prior to the addition of other reactants.

25. The process of claim 1, wherein the Compound A1 and the aqueous solvent are mixed prior to the addition of other reactants.

26. The process of claim 1, wherein Compound 1a**, Compound A1, the aqueous solvent and the catalytic amount of acid are in a mixture and the reaction mixture is stirred at a temperature of about 40° C., then heated to a temperature of about 65° C.

27. The process of claim 26, wherein a first portion of about 20% of the total amount of Compound A1 is added to a mixture of Compound 1a** and the aqueous solvent and the resulting reaction mixture is stirred at a temperature of about 40° C.; then, a second portion of about 40% of the total amount of Compound A1 is added and the reaction mixture is stirred at a temperature of about 40° C.; and, a third portion of about 40% of the total amount of Compound A1 is added and the reaction mixture is stirred at a temperature of about 40° C., then heated to a temperature of about 65° C.

28. The process of claim 1, wherein the Compound A2 is isolated as a free base or as a mono-acid salt.

29. The process of claim 1, wherein water is optionally removed in Step 2.

30. The process of claim 1, wherein the solvent selected for use in Step 2 should be substantially the same solvent as that chosen for use in Step 1.

31. The process of claim 30, wherein the solvent used in Step 2 of the reaction is selected from isopropanol, 2-methoxy-ethanol, 1-propanol, methanol, ethanol, 1-butanol, THF, 2-Me-THF or acetonitrile.

32. The process of claim 31, wherein the solvent used in Step 2 is selected from isopropanol, 2-methoxy-ethanol, 1-propanol or acetonitrile.

33. The process of claim 32, wherein the solvent used in Step 2 is 2-methoxy-ethanol.

34. The process of claim 1, wherein the Compound A2 is a freebase or a mono-acid salt and the Compound A3 is a freebase, a mono-acid salt or bis-acid salt.

35. The process of claim 1, wherein the Compound A2 is a mono-acid salt and the Compound A3 is a bis-acid salt.

36. The process of claim 1, wherein the Compound A2 mono-acid salt and the Compound A3 bis-acid salt are in about a 1:1 molar equivalent ratio.

37. The process of claim 1, wherein the base used in Step 2 is present in a stoichiometric amount and, wherein said amount varies upon whether the reaction product is a free-base, a mono-acid salt or as a bis-acid salt of Compound A4.

38. The process of claim 37, wherein the base used in Step 2 is present in about 2 molar equivalents.

39. The process of claim 1, wherein the Compound A2 mono-acid salt, the Compound A3 bis-acid salt and the base are in about a 1:1:2 molar equivalent ratio.

40. The process of claim 1, wherein the base used in Step 2 is NaOH or NaHCO$_3$.

41. The process of claim 1, wherein the Compound A4 is obtained as an acid salt precipitate during azeotropic distillation at a temperature in a range of from about 102° C. to about 115° C. and, wherein the distilled liquid is controlled to an amount of about twice the amount of water initially added.

42. The process of claim 41, wherein the Compound A2 mono-acid salt is reacted with the Compound A3 bis-acid salt and the base at a temperature in a range of from about 106° C. to about 113° C.

43. The process of claim 1, wherein Compound A4 is obtained as a freebase, a mono-acid salt or as a bis-acid salt.

44. The process of claim 1, wherein the Compound A4 mono-acid salt is recrystallized from a solvent system selected from 1-propanol and water or isopropanol and water, wherein the solvent is in a ratio with water, and wherein the ratio of solvent:water is about 1:1 (v/v).

45. The process of claim 44, wherein the recrystallization solvent system is 1-propanol and water, wherein 1-propanol is in a ratio with water, and wherein the ratio of 1-propanol:water is about 1:1 (v/v).

46. A process for preparing a Compound 78* mono-hydrochloric acid salt of the formula:

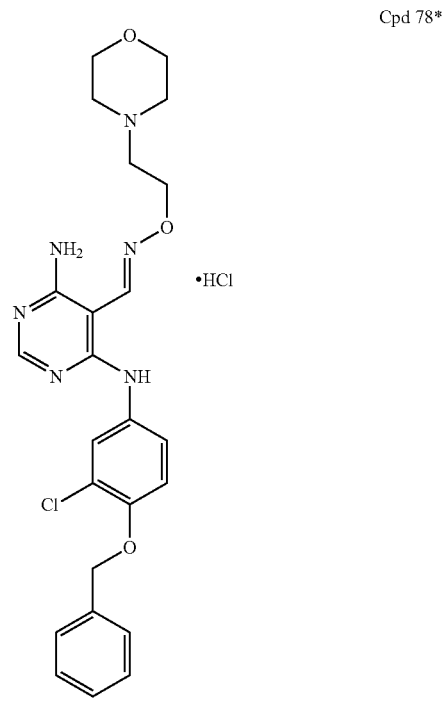

Cpd 78* comprising the steps of:

Step 1. reacting a 4-amino-6-chloro-pyrimidine-5-carbaldehyde Compound 1a, a 4-benzyloxy-3-chloro-phenylamine Compound 1b in an aqueous solvent and a catalytic amount of hydrochloric acid to provide a Compound 1c mono-hydrochloric acid salt:

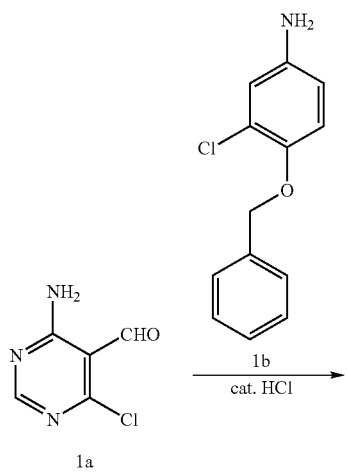

-continued

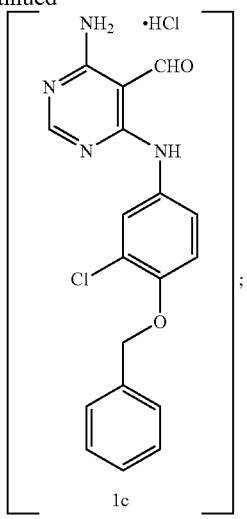

1c

; and

Step 2. reacting the Compound 1c mono-hydrochloric acid salt with a Compound 1d bis-hydrochloric acid salt and a base to provide a Compound 78* mono-hydrochloric acid salt, representative of a compound of Formula (I):

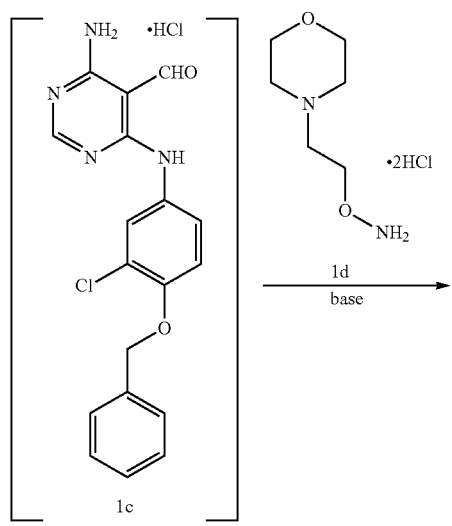

-continued

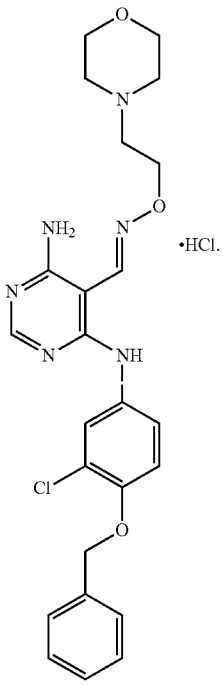

Cpd 78*

47. The process of claim 46, wherein a mixture of stereoisomers of Compound 78* is formed.

48. The process of claim 47, wherein the compound 78* E-isomer is obtained.

49. The process of claim 1, wherein in Step 1 the acid is an acid wherein the anion is a halide that matches the Ra halogen leaving group.

50. The process of claim 2, wherein the mixture further comprises a mixture of stereoisomers consisting of a Compound A4 E-isomer and a corresponding Z-isomer.

51. The process of claim 29, wherein the water is removed by azeotropic distillation in Step 2.

52. The process of claim 47, wherein the mixture of stereoisomers of Compound 78* comprises a mixture of stereoisomers consisting of a Compound 78* E-isomer and a corresponding Z-isomer.

* * * * *